(12) United States Patent
Henniges et al.

(10) Patent No.: US 10,105,481 B2
(45) Date of Patent: Oct. 23, 2018

(54) MEDICAL/SURGICAL IRRIGATOR THAT IS RELEASABLY COUPLED TO AND POWERED BY A POWERED SURGICAL TOOL

(71) Applicant: Stryker Corporation, Kalamazoo, MI (US)

(72) Inventors: Bruce Henniges, Galesburg, MI (US); Adam Dudycha, Paw Paw, MI (US); Benjamin Purrenhage, Kalamazoo, MI (US)

(73) Assignee: STRYKER CORPORATION, Kalamazoo, MI (US)

( * ) Notice: Subject to any disclaimer, the term of this patent is extended or adjusted under 35 U.S.C. 154(b) by 555 days.

(21) Appl. No.: 14/656,798

(22) Filed: Mar. 13, 2015

(65) Prior Publication Data

US 2015/0182685 A1 Jul. 2, 2015

Related U.S. Application Data

(63) Continuation of application No. PCT/US2013/059669, filed on Sep. 13, 2013.

(60) Provisional application No. 61/701,216, filed on Sep. 14, 2012.

(51) Int. Cl.
*A61M 3/02* (2006.01)
*A61M 1/00* (2006.01)

(52) U.S. Cl.
CPC ........ *A61M 3/0258* (2013.01); *A61M 1/0064* (2013.01); *A61M 3/0279* (2013.01); *A61M 3/0283* (2013.01); *A61M 2205/103* (2013.01); *A61M 2205/12* (2013.01); *F04C 2270/041* (2013.01)

(58) Field of Classification Search
CPC .............. A61M 3/0258; A61M 1/0064; A61M 3/0279; A61M 2205/12; A61M 2205/103
See application file for complete search history.

(56) References Cited

U.S. PATENT DOCUMENTS

| | | |
|---|---|---|
| 5,046,486 A | 9/1991 | Grulke et al. |
| 5,269,750 A | 12/1993 | Grulke et al. |
| 5,348,535 A | 9/1994 | Cucin |

(Continued)

FOREIGN PATENT DOCUMENTS

| | | |
|---|---|---|
| CN | 2051507 U | 1/1990 |
| CN | 1064403 A | 9/1992 |

(Continued)

OTHER PUBLICATIONS

PCT "International Search Report and Written Opinion" for PCT/US2013/059669, dated Nov. 2013.

(Continued)

*Primary Examiner* — Bradley J Osinski
(74) *Attorney, Agent, or Firm* — Howard & Howard Attorneys PLLC

(57) ABSTRACT

An irrigator that is powered by a surgical tool capable of driving an implement. The irrigator includes a pump contained in a pump housing adapted for attachment to the tool. The irrigator includes a tip assembly connected to the pump by a flexible supply tube. Thus the tip assembly can be position against tissue against which the irrigating fluid is to be applied without having to likewise position the tool and the pump.

24 Claims, 16 Drawing Sheets

(56) References Cited

U.S. PATENT DOCUMENTS

| | | |
|---|---|---|
| 5,395,312 A | 3/1995 | Desai |
| 5,779,702 A | 7/1998 | Fard |
| 5,941,851 A | 8/1999 | Coffey et al. |
| 6,027,502 A | 2/2000 | Desai |
| 6,099,494 A * | 8/2000 | Henniges ............ A61M 1/0064 601/161 |
| 6,358,224 B1 | 3/2002 | Tims et al. |
| 6,746,419 B1 | 6/2004 | Arnett et al. |
| 7,638,958 B2 | 12/2009 | Philipp et al. |
| 2002/0022797 A1 | 2/2002 | Suh |
| 2006/0093989 A1 | 5/2006 | Hahn et al. |
| 2010/0049119 A1 | 2/2010 | Norman et al. |
| 2010/0317998 A1* | 12/2010 | Hibner ............... A61B 10/0275 600/567 |

FOREIGN PATENT DOCUMENTS

| | | |
|---|---|---|
| CN | 1347738 A | 5/2002 |
| CN | 102137689 A | 7/2011 |
| JP | 2001204732 A | 7/2001 |
| JP | 2006500998 A | 1/2006 |
| WO | 2004028351 A2 | 4/2004 |

OTHER PUBLICATIONS

"Stryker 203 OrthoTec Maintenance Manual & Operating Instructions", pp. 3-5, May 1987.

English language abstract and machine translation retrieved from Espacenet on Oct. 23, 2017 for CN2051507U.

English language abstract and machine translation retrieved from Espacenet on Oct. 23, 2017 for CN1064403A.

English language abstract retrieved from Espacenet on Oct. 23, 2017 for CN1347738A, which was also published as US20020022797A1.

English language abstract retrieved from Espacenet on Oct. 23, 2017 for CN102137689A, which was also published as US20100049119A1.

English language abstract retrieved from Espacenet on Oct. 23, 2017 for JP2001204732A, which was also published as U.S. Pat. No. 6,358,224B1.

English language abstract retrieved from Espacenet on Oct. 23, 2017 for JP2006500998A, which was also published as WO2004028351A2.

* cited by examiner

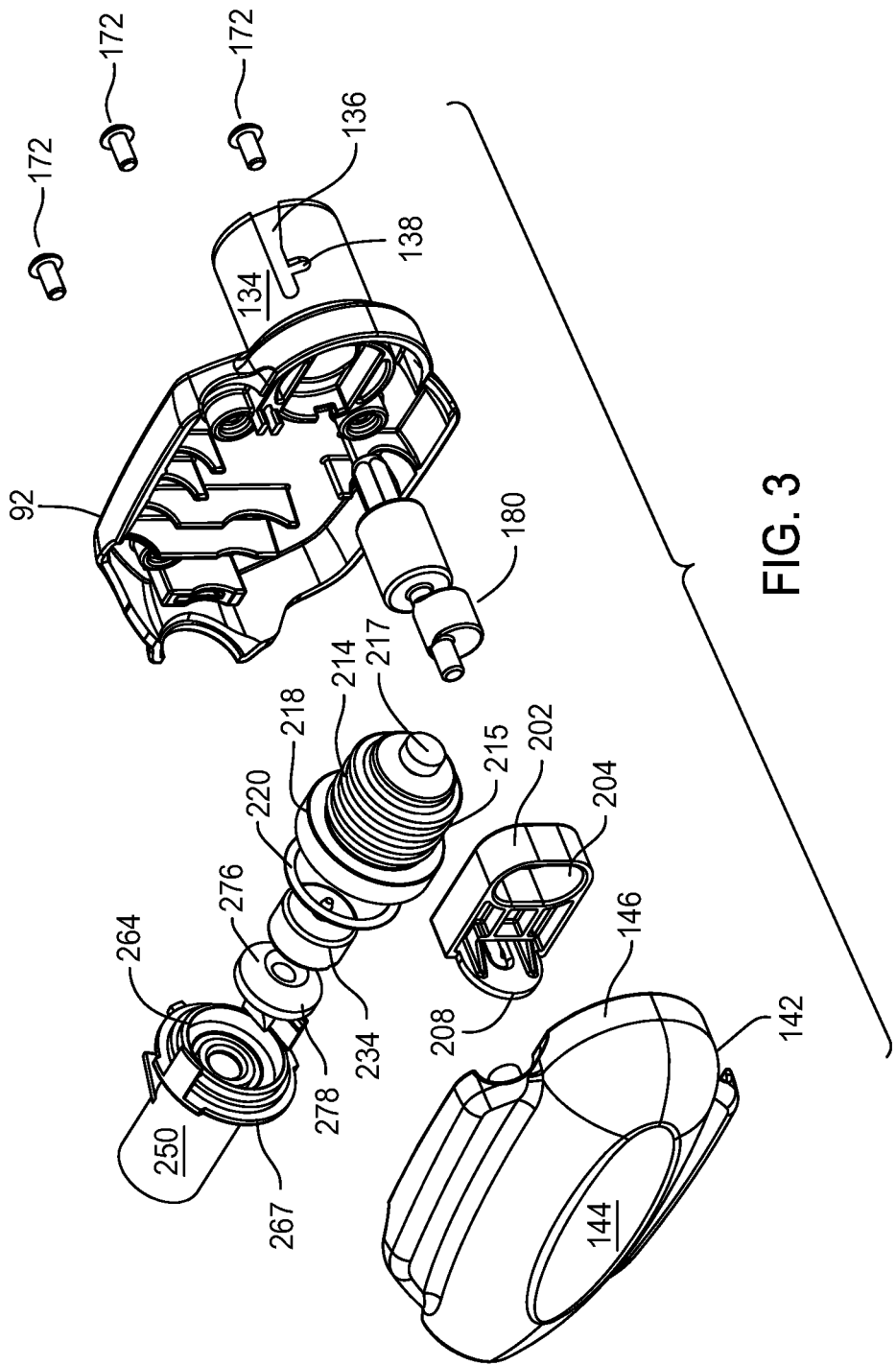

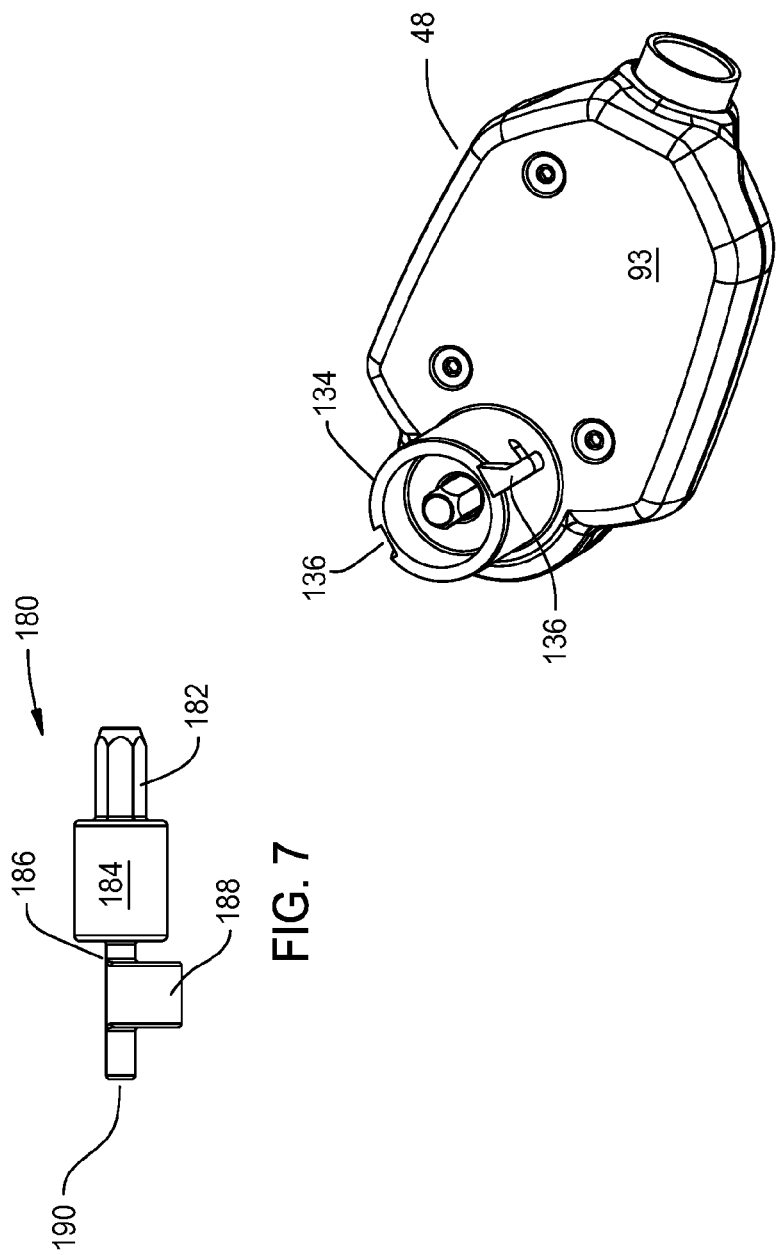

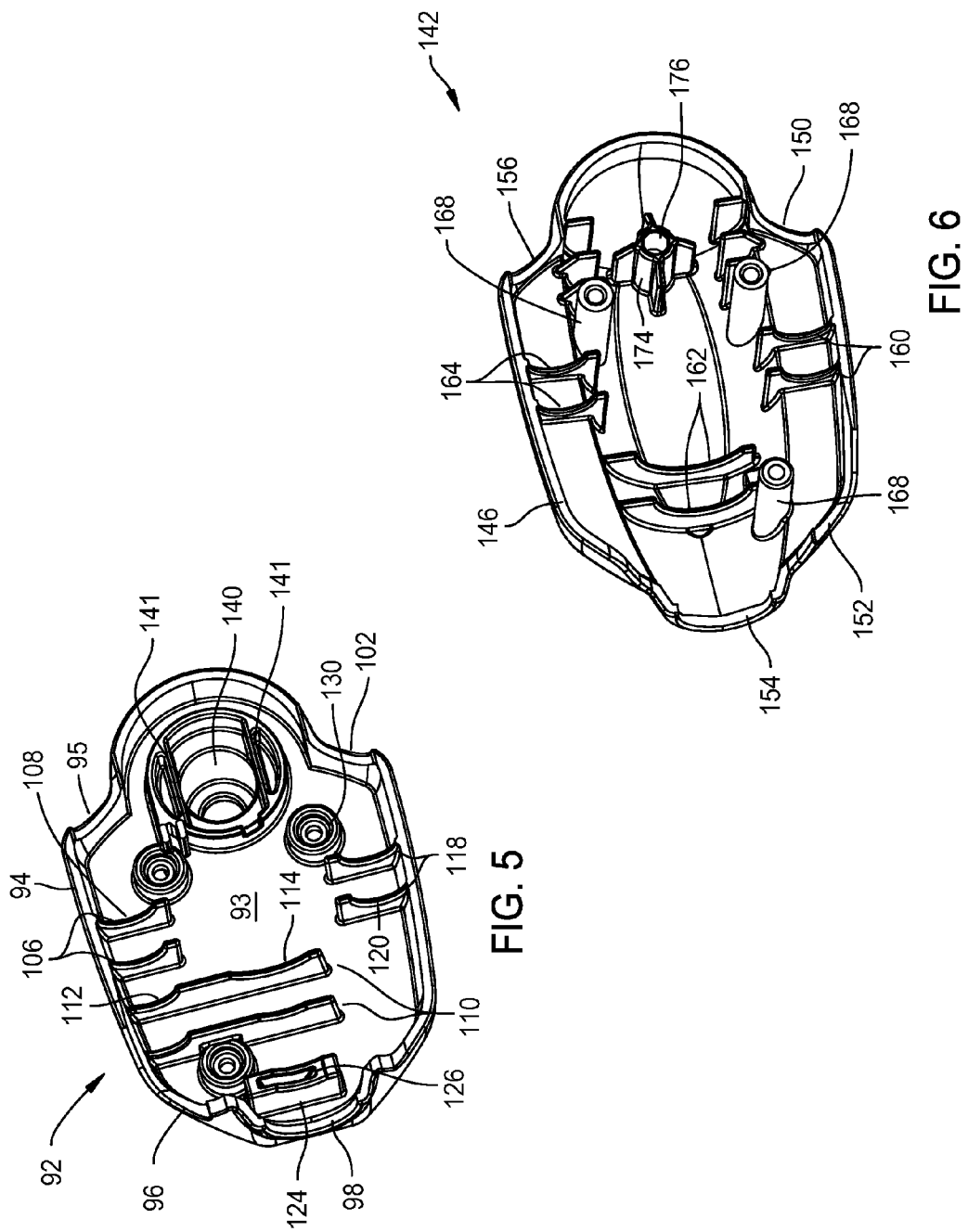

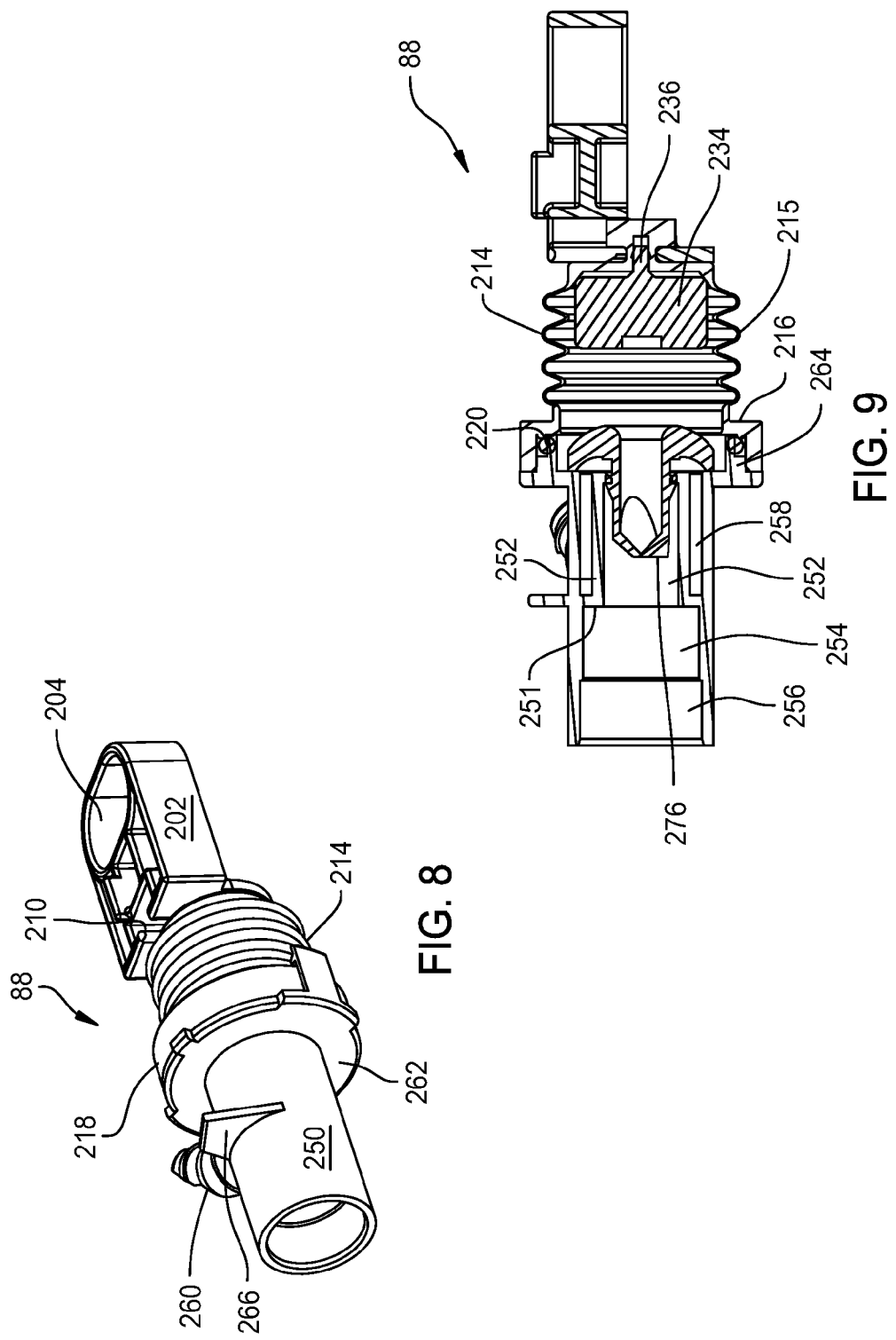

MEDICAL/SURGICAL IRRIGATOR THAT IS RELEASABLY COUPLED TO AND POWERED BY A POWERED SURGICAL TOOL

FIELD OF THE INVENTION

This invention relates generally to medical/surgical irrigators. More specifically this invention is related to a medical surgical irrigator assembly that, in addition to an irrigator, includes a powered surgical tool that actuates the pump integral with the irrigator.

BACKGROUND OF THE INVENTION

In many surgical and medical procedures, an irrigator is employed to deliver fluid to a particular location on or in the body of a person receiving medical attention. For example, during orthopedic surgery, an irrigator is employed to deliver pressurized pulses of water or saline solution to an exposed surface of the bone in order to clean the bone. There are also some non-surgical procedures performed which likewise make it desirable to apply pulses of water to a specific site on an individual's skin. Thus, if an individual is suffering from some type of bed sore or some other type of skin wound, it is a common practice to use an irrigator to clean the wound prior to applying a dressing to the wound.

A common type of medical/surgical irrigator includes a handpiece to which a tip assembly is selectively attached. Inside the handpiece is a small pump that periodically delivers a quantity of pressurized fluid. Also internal to the handpiece is a motor that drives the pump. The fluid is discharged through a discharge tube integral with the tip assembly to the selected site on or in the patient. These irrigators deliver fluid in pressurized pulses for two reasons. One reason is that fluid pulses quickly strike the site to which they are applied and leave the site; this action fosters the desirable removal of debris from the site. Secondly, the discrete fluid pulses do not obstruct the view of the site as much as it can be obstructed when exposed to a continuous flow of pressurized fluid.

Most irrigator handpieces, in addition to having a conduit through which the sterile fluid is discharged, have a conduit through which the discharged fluid is removed from the site to which it is applied. Typically, the fluid is initially withdrawn from the site through a suction tube, also part of the tip assembly. The fluid, as well as any debris in the fluid stream, then flow through a conduit integral with the handpiece. The handpiece suction conduit is connected to a second suction tube that is connected to a suction system separate from the irrigator. Thus, given their ability to essentially simultaneously clean a site on a patient and remove the debris generated by the cleaning process, it should be readily apparent why irrigators have become useful tools for facilitating many medical and surgical procedures. One such irrigator is disclosed in the Applicant's U.S. Pat. No. 6,099,494 PULSED IRRIGATOR USEFUL FOR SURGICAL AND MEDICAL PROCEDURES, the contents of which are explicitly incorporated herein by reference.

Many available medical/surgical irrigators work well for the purposes for which they are designed. One particular disadvantage is associated with the cost of providing these irrigators. For an irrigator to be reusable, it must be able to withstand the rigors of autoclave sterilization. In an autoclave sterilization the irrigator would be subjected to an atmosphere saturated with water vapor (steam) at a temperature of 110° C. or more and at a pressures of 180 kPA and higher. It is expensive to provide an irrigator with internal components able to function after being placed in this type of environment. Furthermore, it has proven difficult to clean, decontaminate and sterilize the conduits integral with an irrigator through which the irrigating fluid is discharge and the fluid and waste extracted by the suction process is withdrawn. Accordingly, presently many irrigators are provided as single-use disposable units. These units have proven costly to manufacture because they include both a pump and a motor that drives the pump.

One solution to reducing the costs of these irrigators is to provide a console with the irrigators. Internal to the console is a motor. The motor drives a pump. Since this console is located outside of the sterile field, the console and its components are not subjected to the rigors of autoclave sterilization. The irrigator, essentially a handpiece to which a tip is attached, is removably coupled to the console by a set of tubes. These pumpless and motorless irrigators are less expense to provide than irrigators that include these components. Some of these irrigator systems actually predate irrigators that include pumps and motors. One such assembly is disclosed in the Applicants' Assignee's U.S. Pat. Nos. 5,046,486 and 5,269,750 the contents of which are explicitly incorporated herein by reference.

These irrigators have their own disadvantages. Specifically, these irrigators require their own consoles. Thus to use one of these irrigators it is necessary to add another unit, an irrigator console to the surgical suite. Having to provide this console adds to the cost of outfitting the operating room. Alternatively, a facility can have less irrigator consoles than it has operating rooms/treatment rooms in which an irrigator may be used. This would then require the medical personnel to ensure that, prior to the start of the procedure in which an irrigator will be used to ensure that the console for the irrigator is in place. If the console is not in place, effort must be spent setting up the console prior to the start of the procedure.

It has been suggested to use a powered surgical tool to power a medical irrigator. One known system includes an adapter that extends forward from the body of the tool. The adapter includes a gear assembly that converts the rotary motion of the shaft integral with the tool motor into a reciprocating motion. A pump is removably attached to this adapter. This system eliminates the need to provide each irrigator with its own motor. However the known version system is believed to be relatively heavy and bulky. For example, the power tool, which must be held and positioned, typically with just one hand, can weigh in excess of 1 kg. Having to hold and position this tool with a single hand can make the system ergonomically difficult to use. Further, if the practitioner needs to hold the tool steady, such as at specific surgical or wound site for anything more than one or two minutes, the practitioner can start to experience muscle strain and fatigue.

SUMMARY OF THE INVENTION

This invention is related to a new and useful medical/surgical irrigator assembly. The irrigator assembly of this invention includes an irrigator handpiece that is economical to provide and that does not require a console designed solely or primarily for use with the irrigator.

The irrigator assembly of this invention includes a handpiece. Also part of the irrigator assembly of this invention is a pump unit. Typically, the pump unit is contained in a pump housing that is separate from the handpiece. The assembly of this invention also includes a powered surgical tool that includes a motor. The tool is the type of tool able to drive some type of cutting implement that is typically applied directly to a surgical site. The pump unit and more particularly the pump housing is designed to be releasably attached to the powered surgical tool. When the pump housing is so attached to the surgical tool, the motor internal to the tool drives the pump.

To drive the cutting implement, the powered surgical tool has a coupling assembly. The coupling assembly includes components capable of releasably holding the cutting implement to the tool so the tool motor will drive the implement.

In some versions of this invention, the pump housing is designed to be fitted to the surgical tool so that housing can be in one of a plurality of different orientations relative to a fixed point on the tool. This features facilitates the configuration of the irrigator assembly of this invention so the components are positioned relative to each other in an arrangement that is most ergonomic and/or minimal inconvenient for the particular practitioner and/or the procedure in which the assembly is to be used.

An alternative version of the irrigator assembly of this invention includes a transmission and a pump cassette. The transmission fits on top of the powered surgical tool. The pump cassette is disposed on top of the transmission. The rotational moment from a spindle internal to the tool is, by the transmission converted into a reciprocating motion. The reciprocating motion drives a pump internal to the cassette.

BRIEF DESCRIPTION OF THE DRAWINGS

The invention is pointed out with particularity in the claims. The above and further features and benefits of this invention are understood from the following Detailed Description taken in conjunction with the accompanying drawings in which:

FIG. 3 is an exploded view of the pump of this invention;

FIG. 4 is a perspective view of the shell of the pump;

FIG. 5 is a perspective view of the inside of the pump proximal shell;

FIG. 6 is a proximal view of the inside of the pump distal shell;

FIG. 7 is a side plane view of the pump drive shaft;

FIG. 8 is a perspective view of the actual pump unit internal to the pump;

FIG. 9 is a cross sectional view of the pump unit;

DETAILED DESCRIPTION

I. First Embodiment

Figure 1:
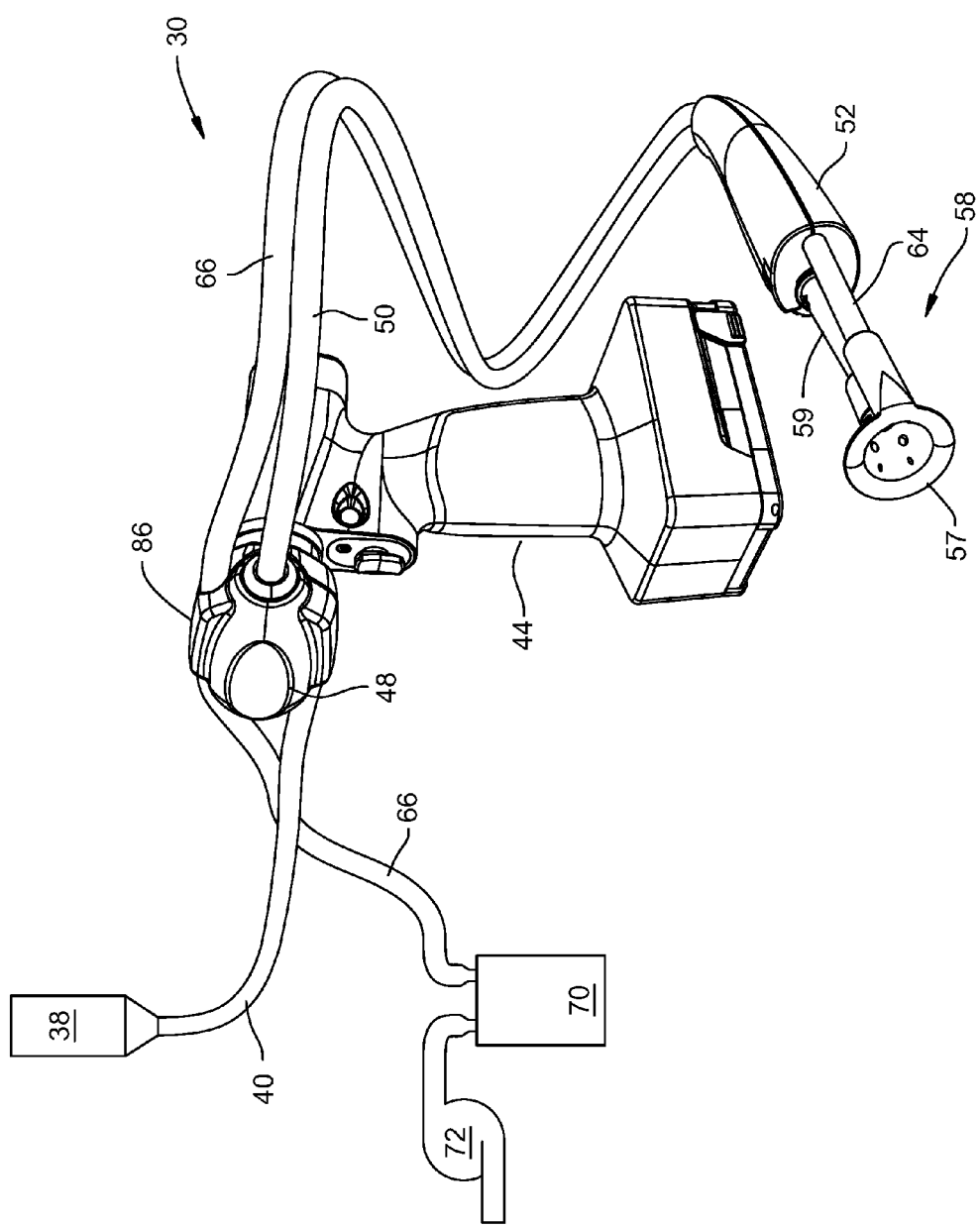
FIG. 1 depicts the major components of the medical/surgical irrigator assembly of this invention.

FIG. 1 depicts the basic components of a medical/surgical irrigator assembly 30 of this invention. Assembly 30 includes a wand 52. A tip assembly 58 is removably attached to and extends forward from the distal end of the wand 32. (In this document "distal" is understood to mean away from the front of the practitioner holding the wand, towards the site on the patient to which the wand is directed. "Proximal" means towards the front of the practitioner, away from the site on the patient to which the wand is directed.) The tip assembly includes a discharge tube 59. Irrigating fluid flow from a source 38 through a pair of supply tubes 40 and 50 to the wand 52. The irrigating fluid flows out of the wand into the tip assembly 58. The fluid is discharged out of the distal end of the tip assembly discharge tube 59 to the on-patient site to which the practitioner applies the tip assembly. A spray shield 57, not part of the present invention, is disposed over the distal end of tip assembly 58.

A pump 48 is located between supply tubes 40 and 50. Pump 48 supplies the motive power that pumps the irrigating fluid through tube 50, the wand 52 and out of the tip assembly 58. The pump 48 is removably attached to a powered surgical tool 44. Tool 44 can be used to drive a cutting implement used to accomplish a medical/surgical task. Internal to tool 44 is a motor 46. These implements include reamers, wire drivers, a drill or a saw blade. Motor 46 supplies the mechanical energy that actuates pump 46.

Tip assembly 58 includes a suction tube 64. Suction tube 64 is approximately parallel with and located above discharge tube 59. Webs 63 (identified in FIG. 10) hold tubes 59 and 64 together. Tip assembly suction tube 64 is connected to a suction tube 66 the distal end of which is disposed in wand 52. Suction tube 66 extends proximally from the wand 52. The proximal end of the suction tube is connected to a device 72 that draws a suction. When irrigator assembly 30 is used device 72 is typically actuated. Once the fluid discharged from the tip assembly strikes the tissue against which the tip assembly is applied, suction device 72 draws the fluid away from tissue through suction tubes 64 and 66. The suctioned fluid is collected in a container 70.

Figure 2:
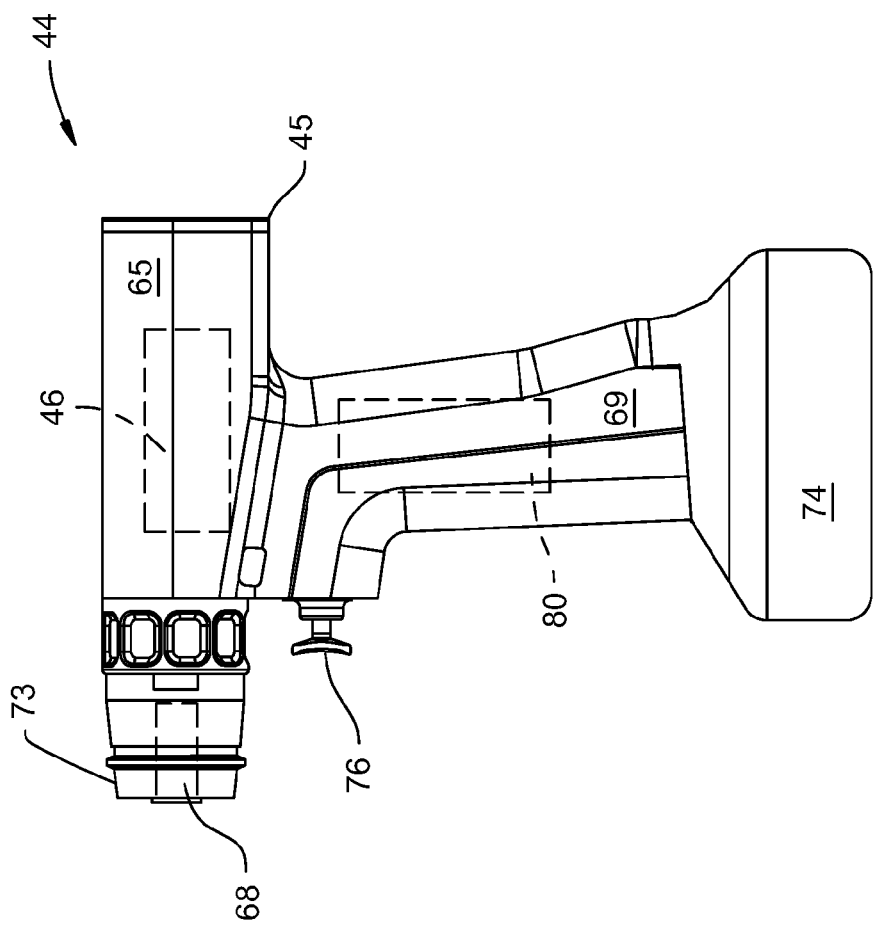
FIG. 2 depicts a powered surgical tool.

Powered surgical tool 44 is a sterilizable, reusable powered surgical tool. Here, "sterilizable" means the tool is able to withstand the rigors of a sterilization process that allows the product to be used for a medical or surgical process. One such sterilization process is an autoclave sterilization processor wherein the product being sterilized is exposed to supersaturated water vapor (steam) at a temperature in excess of 110° C., at a pressure of 180 kPa and higher. As seen in FIG. 2, tool 44 includes a tool body 45. (There are some aesthetic differences between the tool body of the tool of FIG. 1 and the tool of FIG. 2.) In the depicted version of the invention, tool body 45 is pistol shaped. The body has a barrel 65 and a handgrip 69 that extends downwardly from the barrel. Motor 46, represented as a dashed line cylinder, is disposed in the barrel 65. A drive spindle 68, shown in dashed lines, extends forward from the motor 46. In one version of the invention, spindle 68 has a closed end bore that extends inwardly from the distally directed face of the spindle. The bore of the drive spindle 68, in cross section, is hexagonal.

Tool 44 includes a coupling assembly. In FIG. 2, the coupling assembly is represented by a sleeve 73 that extends forward from the distally directed face of body barrel 65. In one version of the invention, pins (not illustrated) extend inwardly from opposed inner surfaces of sleeve 73. The pins are also part of the coupling assembly. The drive spindle 68 is accessible through the axial opening through sleeve 73.

The drive spindle 68 and the coupling assembly are collectively configured to releasably receive a cutting implement. The cutting implement may be an actual device that is applied to a site on the patient to perform a medical/surgical task. One such cutting implement is a reamer shaft. Alternatively, the cutting implement may be some sort of front end attachment. The attachment functions as an intermediate transmission unit that transmits the rotary motion of the tool drive spindle 68 to the actual cutting implement that is applied to the patient. One such front end attachment is a wire driver. As its name implies the wire driver drives, advances, a wire distally forward so the wire can be secured into bone. Drive spindle 98 is configured to releasably be coupled to and drive the cutting implement. The coupling assembly releasably holds the cutting implement to the tool 44 and, more specifically, the driven portion of the cutting implement to the drive spindle 68.

A battery 74 is removably attached to the butt end of tool handgrip 69. Battery 74 is supplies the electrical energy that powers tool motor 46. A trigger 76 is moveably mounted to the handpiece body 62. In the depicted version of the invention trigger 76 extends forward from a distally directed face of the handgrip 69 a short distance below barrel 65. Disposed inside the handgrip is a control module 80. Both the motor windings and the battery 74 are connected to the control module 80. Control module 80 also includes components that monitor the displacement of trigger 76. The practitioner actuates the tool motor by selectively depressing trigger 76. In response to the displacement of the trigger, the control module selectively applies current from the battery to the motor so as to actuate the motor. One such handpiece is disclosed in the Applicant's Assignee's U.S. Pat. No. 7,638,958, the contents of which are incorporated herein by reference. Battery 74, like tool 44, can withstand the rigors of autoclave sterilization. The exact structure of the tool, including its coupling assembly and the battery 74 are not part of the present invention.

From FIG. 3 it can be seen that the pump 48 includes a housing 86. Internal to housing 86 is the actual pump unit 88 (FIG. 8). Housing 86 consists of first and second shells 92 and 142, respectively. Both shells 92 and 142 are formed from plastic such as ABS. Shells 92 and 142 both can approximately be considered an oval shape. The proximally directed shell, shell 92, now described by reference to FIGS. 3, 4 and 5, includes an outer panel 93. A rim 94 extends distally forward around the outer perimeter of panel 93. Proximal shell 92 is formed so that there are a number of arcuately shaped indentations in rim 94. A first indentation, indentation 95, is located in one section of the rim where end section of the rim curves into a side section. A second indentation, indentation 96, is formed in the rim so as to be on the same side of shell 92 and at the opposite end of the shell from where indentation 95 is located. A third indentation, indentation 98, is formed in end of the rim adjacent second indentation 96. A fourth indentation, indentation 102 is located in the rim 94 so as to be located at the same end of shell 92 as first indentation 95 and on the opposite side of the shell as the first indentation 95.

A number of webs extend distally forward from the inner surface of panel 93. Specifically, two parallel webs 106 extend inwardly from the panel and one of the inner surfaces of rim 94 along one of the side surfaces of the shell 92. Each web 106 is formed to have an arcuate cutout 108 (one identified). Cutouts 108 are generally aligned with rim indentations 95 and 96. Two parallel webs 110 extend inwardly from the rim such that webs 110 are located along the same side of the shell as webs 106. Webs 110 are longer in length than the adjacent webs 106. Each web 110 is defined to form first and second arcuate cutouts 112 and 114, respectively. Each web cutout 112 is located close to the adjacent section of the rim 94 from which the web 106 extends. Web cutouts 112 are generally aligned with the cutouts 108 integral with the adjacent webs 110. Web cutouts 114, (one identified) which are generally aligned with each other are located proximal to the center of shell panel 93 so as to be aligned with rim indentation 98. Two parallel webs 118 extend outwardly from the section of the rim 96 opposite the rim section from which webs 106 extends. Each web 118 is formed to have an arcuate cutout 120. Cutouts 120 (one identified) are generally aligned with rim indentation 102.

Proximal shell 92 is further shaped to have a pylon 124 that is generally rectangular in shape. Pylon 124 is located between the end section of the rim 94 in which third indentation 98 is formed and the adjacent web 110. The pylon 124 is further formed to have an inwardly directed closed end rectangularly shaped slot 126. Shell 92 is further formed so that the distally directed face of pylon 124 has a concave profile, not identified. The concave portion of pylon 124 is generally aligned with rim indentation 98 and cutouts 114 integral with webs 110. Three bosses 130 (one identified) also extend outwardly from the distally directed surface of shell panel 93. Each boss 130 has a multi section bore, not identified. Proximal shell 92 is formed so that the largest diameter section of each boss bore is the most distal one of the bore sections.

A coupling member is formed integrally with and extends outwardly from the proximal shell 92. This coupling member is designed to engage the handpiece coupling feature so the pump housing can be releasably attached to the tool body 62. In the depicted version of this invention, this coupling member is a sleeve 134 that extends proximally outwardly from the outer surface of shell panel 93. Sleeve 134 is shaped to closely slip fit within tool sleeve 73. The outer surface of sleeve 134 is formed to have two diametrically opposed indentations 136 (one seen in FIG. 3). Each indentation 136 extends longitudinally distally forward from the proximal end of the sleeve 134. Each indentation 136 has a detent 138. Indentations 136 and detents 138 are shaped to receive the pins internal to the tool sleeve 73 that are part of the tool coupling assembly.

Shell sleeve 134 is further formed to have a multi-section through bore 140 (FIG. 5) that extends axially through the sleeve. Bore 140 is formed so that the bore section with the smallest diameter is located adjacent the proximal end of the sleeve 134. Above the opening into sleeve bore 140, the proximal shell 92 is shaped to have two parallel ribs 141. Ribs 141 are parallel to and equal spaced apart from the major axis across the proximal shell 92.

Shell 142 is shaped to fit against shell 92. Shell 142 as seen in FIGS. 3 and 6, has an outer panel 144 that is in the form of elongated dome. A rim 146 extends proximally around the outer perimeter of panel 144. When pump 48 is assembled, distal shell rim 146 seats against proximal shell rim 94. Distal shell 142 is shaped so as that there are four arcuately shaped indentations in the rim 146. A first indentation 150 is located so that when the pump is assembled the indentation 150 forms an opening with indention 95 in rim 94. A second indentation 152 is located so that when the pump is assembled the indentation 152 forms an opening with indention 96 in rim 94. A third indentation 154 in rim 146 is located so as to form an opining with the third indentation 98 of rim 94. A fourth indentation 156 is located so that when the pump is assembled the indentation 156 forms an opening with indention 102 in rim 94.

Distal shell 142 is further formed so that six webs extend proximally from the inner surface of shell panel 144. Two of the webs, webs 160, are positioned so as to each be in registration with a separate one of the webs 106. Two of the webs, webs 162, are positioned to each be in registration with a separate one of the webs 110. More particularly, each web 162 is in registration with the section of the complementary web 110 that defines the web cutout 114. The remaining two webs, webs 164, are positioned so as to each be in registration with a separate one of the webs 118 integral with proximal shell 92. Each web 160, 162, and 164 is formed with an arcuate cutout, (cutouts not identified). The cutouts integral with webs 160, 162, and 164 are positioned to be contiguous with the cutouts 108, 114, and 120, respectively integral with the proximal shell 92.

Three posts 168 extend proximally from the inner face of shell panel 144. Posts 168 are positioned so that when pump 48 is assembled, each post 168 seats in the largest diameter section of the bore of a separate one of the proximal shell bosses 130. Each post 168 is formed with a closed end bore 170. Upon assembly of the pump fasteners 172 extend through bosses 130 into posts 168 to hold shells 92 and 142 together.

A boss 174 also extends proximally from the inner face of shell panel 144. Boss 174 is positioned so that when the pump is assembled, boss is centered on the extension of the axial line through sleeve bore 140. Boss 174 is formed to have a closed end axially extending bore 176. Not identified are the reinforcing flanges that extend from shell panel 144 to the outer surface of boss 174.

Pump 48 includes a single-piece drive shaft 180 best seen in FIGS. 3 and 7. Drive shaft 180 is formed from a plastic such as 10% glass filled nylon. The drive shaft 180 is shaped to have a foot 182. The foot is shaped to be releasably coupled to the tool spindle 68. In the version of assembly 30 wherein the tool spindle has a hexagonal bore, drive shaft foot 182 is, in cross section hexagonal in shape and dimensioned to closely slip fit in the drive spindle bore. Extending distally from foot 182, drive shaft 180 has a torso 184. Torso 184 is cylindrical in shape and coaxial with foot 182. Torso 184 is dimensioned to closely fit in one of the sections of sleeve bore 140. Torso 184 functions as a low friction interface between the rotating drive shaft 180 and the static pump proximal shell 92.

A neck 186 extends distally forward from drive shaft torso 184. Neck 186 is coaxial with and smaller in diameter than torso 184. Distally forward of neck 186, the drive shaft 180 is formed to have a cylindrical head 188. Head 188 has a diameter slightly less than that of torso 184, greater than that of neck 186. The drive shaft 180 is shaped so that head 188 has a longitudinal axis that is parallel with and offset from the common longitudinal axis of the foot 182, torso 184 and neck 186. A cylindrical, pin-like nose 190 extends distally forward from head 188. Nose 190 has a diameter less than that of head 188. In some versions of the invention, the nose 190 has a diameter equal to that of the neck 186. The longitudinal axis of the nose is aligned with the common longitudinal axis of the foot 182, torso 184 and neck 186.

When the pump 48 is assembled, shaft foot 182 is axially disposed in sleeve 134. Drive shaft head 188 is disposed in the space between shells panels 93 and 144. The drive shaft nose 190 is rotatably disposed in the bore 176 internal to distal shell boss 174.

A yoke 202, seen best in FIGS. 3 and 8, is slidably disposed between shells 92 and 142. More particularly, yoke 202 is slidably disposed between ribs 141 integral with proximal shell 92. Yoke 202 is formed from a set of webs and plates that, with one exception below, are not identified. The yoke is formed to define an oval opening 204. Pump 48 is constructed so that drive shaft head 188 seats within and can move within yoke opening 204.

Opposite the opening 204, yoke has an end plate 208. A notch 210 extends inwardly from one side edge of end plate 208.

Spaced longitudinally away from the yoke end plate 208, pump 48 has a static tube 250, now described by reference to FIGS. 8 and 9. Tube 250 is formed from plastic and is cylindrical in shape. Tube 250 is formed to have a number of different sections. These sections define three coaxial bores 252, 254, and 256 that collectively extend through the tube. Bore 252 is the bore closest to the yoke 202. Bore 256 is the bore that forms the open end of the bore adjacent the opening defined by shell indentations 98 and 154. Bore 254 is larger in diameter than bore 252. Bore 256 is larger in diameter than bore 256.

Tube 250 is further formed to have a step 251 and an inner sleeve 257. Step 251 and inner sleeve 252 define bore 252. Step 251 and inner sleeve 252 define an annular channel 258 that extends around and is isolated from the coaxial bores 252, 254 and 256. Annular channel 258 opens towards yoke 202. Not identified is a small step that extends inwardly from the inner sleeve 252. This step is located adjacent the open end of bore 252. A fitting 260 extends diagonally away from tube 250. Fitting 260 opens into annular channel 258.

A lip 262 extends radially outwardly from the main cylindrical body of the tube. Lip 262 is located around the end of the main body of the tube closes to yoke 202. An annular ring 264 extends outwardly from lip 262 towards yoke 202. Ring 264 is located inwardly from the outer perimeter of lip 262.

A tab 266 extends outwardly from the main cylindrical body of tube 250. Tab 266 is seated in a plane that is perpendicular to the longitudinal axis of the tube 250. When pump 48 is assembled, tab 266 seats in proximal shell pylon slot 126. The seating of tab 266 in the pylon slot 126 holds tube 250 as well as the components attached to the tube to proximal shell 92. When the tube 250 is disposed in the pump housing the end of the tube extends out of the opening defined by shell indentations 98 and 154.

A duck billed valve 276 is seated in tube bore 252. Valve 276 is arranged so that the open end of the valve is directed towards the yoke 202. The lips of the valve 276 are directed towards tube bore 254. Valve 276 has a base 278 that extends radially outwardly from the valve around the open end of the valve. Base 278 is curved in cross section. The outer perimeter of the valve base 278 abuts tube lip 262. The components of the pump are arranged such that there is a small annular void space between tube lip 262 and valve base 278. Tube annular channel 258 opens into this void space.

A bellows 214 extends between yoke 202 and tube 250. Bellows 214 is formed from a flexible thermoplastic and has a cylindrical main body 215 formed with circumferentially extending pleats (not identified). Bellows body 215 has a closed end adjacent yoke end plate 208. Bellows body 215 has an open end directed to tube bore 252. A lip 216 extends radially outwardly and circumferentially around the open end of bellows body 215. A ring 218 extends from the outer perimeter of lip 216 towards tube 250. More particularly, bellows ring 218 extends snuggly around ring 264 integral with tube 250. An O-ring 220 is disposed over the outer surface of tube ring 264. The O-ring 220 is pressed between bellows lip 216 and tube ring 264. The O-ring 220 thus contributes to the seal between the bellows 214 and tube 250.

A button 217 extends outwardly from the closed end of bellows 214. Button 217 fits into the notch 210 integral with the yoke end plate 208 to hold the bellows 214 to the yoke 202.

A solid cylindrical head 234 is disposed in the bellows body 215. A small crown 236 extend forward from the head. The crown 236 extends into a void space in yoke button 217 (void space not identified). The head thus reciprocates with the reciprocation of the bellows 214.

Supply tube 40 extends from the irrigating fluid source 38 into the pump housing through the opening defined by indentations shell indentations 102 and 156. Immediately proximal to the distal end of the tube 40, the suction tube is compression held to the housing in the spaces defined by the cutouts integral with shell webs 118 and 164. The distal end of supply tube 40 is seated over tube fitting 260. The proximal end of supply tube 50 is fitted in tube bore 256. Supply tube 50 extends out of tube bore 256 and out of the pump housing through the opening defined by indentations 98 and 154.

Suction tube 66 extends through the pump housing. Proximally from wand 52, the suction tube 66 extends into the pump housing through the opening defined by shell indentations 96 and 152. Within the pump housing, the suction tube 66 is disposed within cutouts 108 integral with webs 106 of the proximal sell 92 and the cutouts integral with the opposed webs 160 of distal shell 142. Suction tube 66 extends out of the pump housing through the opening defined by indentations 95 and 150.

Supply tube 50 is formed from PVC tubing. In some versions of the invention, tube 50 resists radial expansion. This type of tube has a relatively high modulus of elasticity. Material hardness is generally portion to the modulus of elasticity for tubing. Accordingly it is desirable to provide a supply tube 50 that has a hardness of at least Shore A 80 and more often at least Shore A 100.

Figure 10:
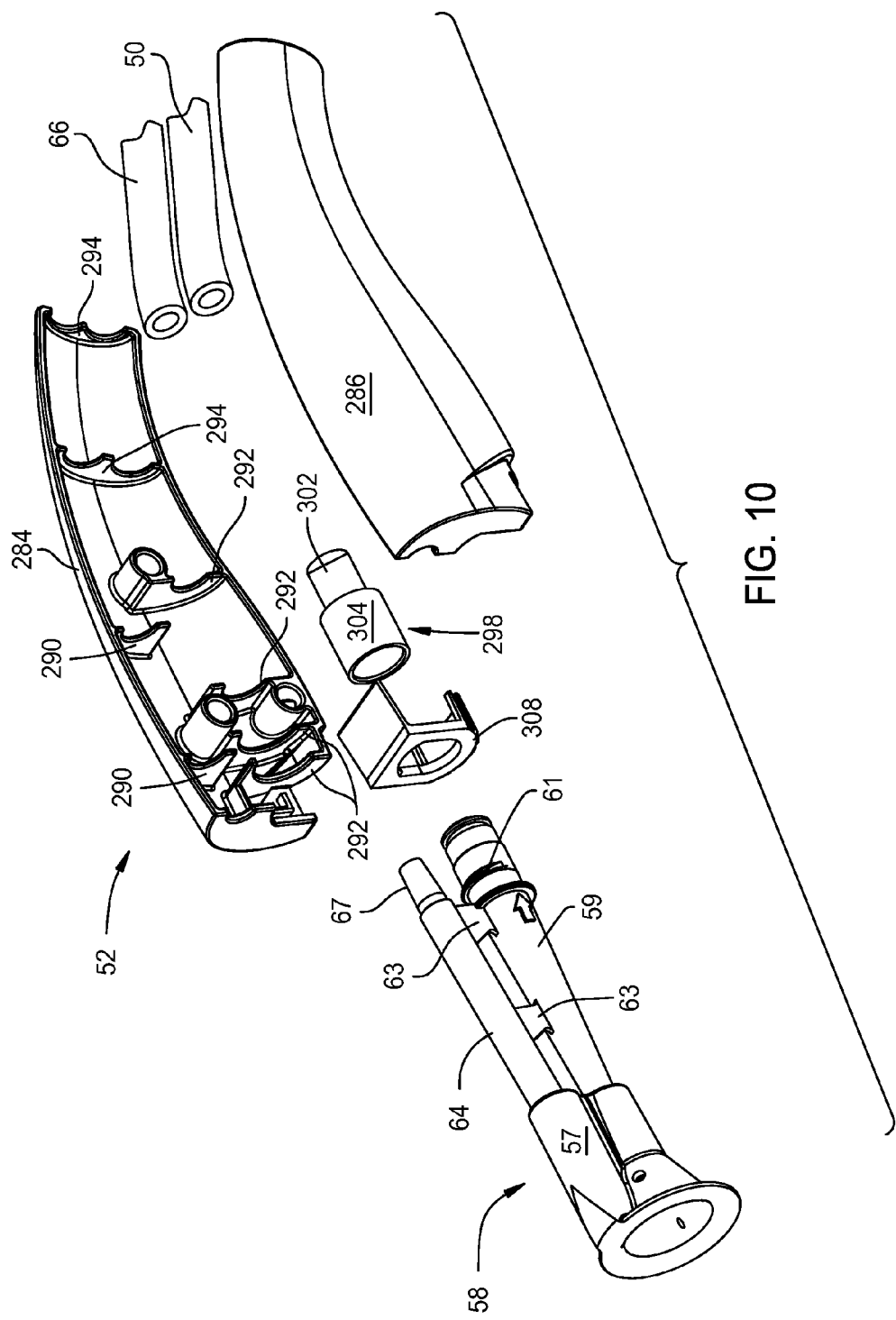
FIG. 10 is an exploded view of the wand and tip assembly.
Figure 11:
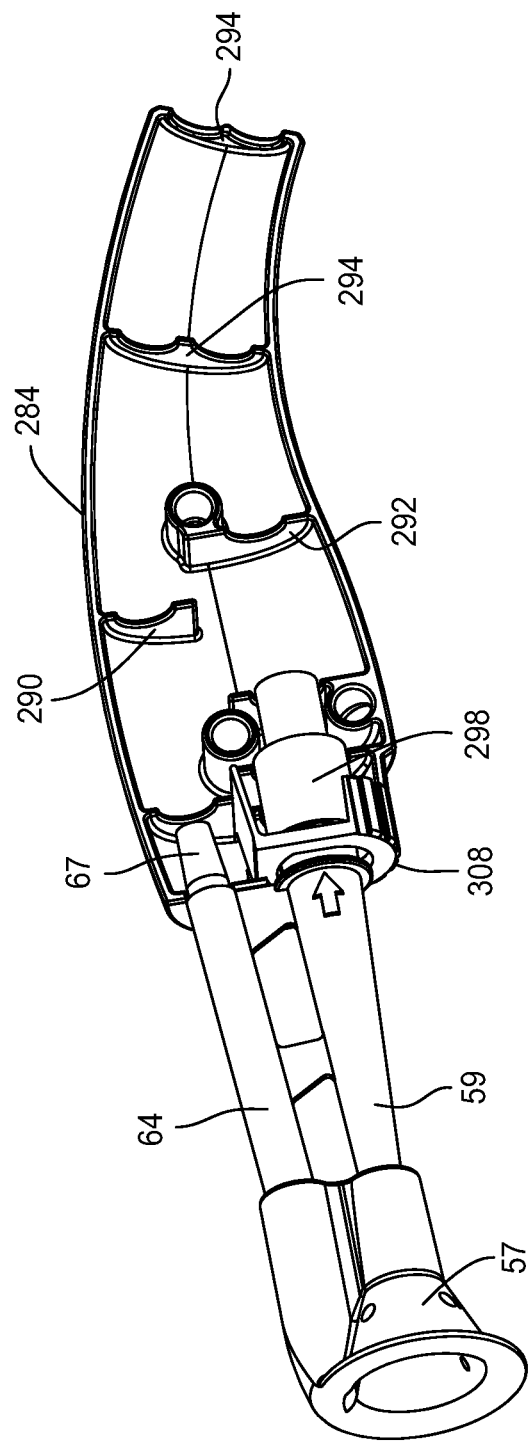
FIG. 11 is a side perspective view of the wand and tip assembly with one of the wand housing shells removed.

As seen by reference to FIGS. 10 and 11, wand 52 is constructed from first and second shells 284 and 286, respectively. Internal to the shells 284 and 286 are webs 290, 292 and 294. Only the webs 290, 292 and 294 in shell 284 are illustrated. Two longitudinally spaced apart webs 290 are located towards the top of each shell 284 and 286. Each web 290 is formed with a cutout (not identified). Four webs 292 are located towards the bottom of each shell 284 and 286. Two of the webs 292 are located adjacent the distal ends of the shells. The third web 292 is spaced proximal from the first two webs. The fourth web 292 is spaced proximally from the third web 292. There are two webs 294 each of which extends top to bottom within the shell 284 and 286. A first web 294 forms the proximal end of the shell 284 and 286. A second web 294 is located forward of the most proximal web and distal to the webs 290 and 292.

Each web 294 is formed with two cutouts (not identified). Also not identified are the bosses with bores internal to shells 284. While not illustrated it should be understood that shell 286 is formed with complementary bosses with bores. Not illustrated are the threaded fasteners that extend through these bosses so as to hold shells 284 and 286 together.

A fitting 298 is seated in the forward end of the wand housing. The fitting 298 is in the form of two contiguous rigid tubes. The fitting comprises a proximal tube 302 and a distal tube 304. Distal tube 304 has outer and inner diameters greater than the respective diameters of the proximal tube 302. Fitting 298 seats in the cutouts formed in webs 292. The distal end of the supply tube 50 extends into the proximal end of the wand housing. The supply tube 50 is lightly compression secured between webs 294 and the proximal most web 292. The distal end of the supply tube 50 is seated in the bore internal to fitting proximal tube 302. The proximal end of suction tube 66 is disposed in the wand housing. The suction tube 66 is seated in the cutouts integral with webs 290 and the top located cutouts integral with webs 294. Suction tube 66 extends out of the wand housing above supply tube 48.

A tip lock 308 is moveably mounted to the wand 52. More specifically the tip lock 302 is sandwiched between shells 284 and 286. In the depicted version of the invention, the tip lock is located forward of fitting 298. The tip lock 308 contains features that releasably engage complementary features integral with tip assembly 58 so as to releasably hold the tip assembly to the wand 52. In the depicted version of the invention the tip assembly feature that the tip lock 302 engages is an arcuate rib 61 that extends partially circumferentially around the discharge tube 59 forward of the proximal end of the tube. The exact structure of the tip lock is not part of the present invention.

The bore internal to fitting distal tube 304 is dimensioned to receive the proximal end of the tip assembly discharge tube 59. Seals, (not illustrated) may be fitted over the discharge tube 59 or disposed in the distal tube 304. The seals prevent water leakage between the discharge tube 59 and fitting 298. Tip assembly suction tube 64 is formed to have a tapered head 67. The head is dimensioned to seat in the open end of irrigator suction tube 66, the end seated in the distal end of wand 52.

Irrigator assembly 30 of this invention is prepared for use by fitting a tip assembly 58 to wand 52. Supply tube 40 is connected to irrigating fluid source 38. Suction tube 64 is connected to suction device 72. Pump assembly 48 is fitted the powered surgical tool 44. More particularly, this step is performed by inserting housing sleeve 134 in tool sleeve 73. The complementary coupling features of the tool 44 and the housing sleeve 134 releasably hold the pump housing 86 to the tool 44. As a consequence of the fitting of the pump assembly 48 to the tool 44, the pump drive shaft 180 seats in the tool drive spindle 68. Owing to the dimensioning of the components, the pump drive shaft 180 rotates in unison with the tool drive spindle 68.

Once the above steps are completed, irrigator assembly 30 is ready for use The practitioner uses assembly 30 by pressing the tip assembly 58, often the open end of the spray shield 57, against the tissue to which the irrigating solution is to be applied. The practitioner discharges the solution by depressing the tool trigger 76. Upon detection that the trigger 76 has been depressed, the control module 80 actuates the tool motor 46. The resultant rotation of the drive spindle 68 results in a like actuation of the pump drive shaft 180. The rotation of the shaft 180 results in the reciprocation of the pump bellows 214. The reciprocation of the pump bellows results in fluid being drawn into the bellows through supply tube 40, fitting 260 and annular channel 258. The fluid is forced out through supply tube 50. The fluid pumped through supply tube 50 is discharged from the wand 52 through the tip assembly discharge tube 59. Simultaneously, suction is drawn through the tip assembly suction tube 64 and pump suction tube 66. This suction draws the discharge irrigation fluid as well as any waste entrained in the fluid to container 70.

Supply tube 50 being relatively hard is, while flexible, radially stiff (resists radial compression and radial expansion.) Owing to the radial stiffness of the supply tube 50, when a pulse of fluid is discharged from pump 48, the pulse pressure does not appreciably expand the supply tube 50. Thus only a small fraction of the pulse pressure is attenuated in the supply tube 50 as the pulse transits from through tube for discharge out of the tip assembly.

Irrigator assembly 30 of this invention thus performs the irrigation and suction functions of a conventional irrigator. However, unlike many conventional disposable irrigators, assembly 30 does not have a pump motor. Instead, the motor 46 internal to the tool 44 functions as the pump motor. Thus, in comparison to irrigators with their own pumps, it can be more economical to provide irrigator assembly 30 of this invention.

It should further be appreciated that the motor 46 internal to the tool is more powerful than the use-once motor that is typically included with a conventional irrigator. More specifically, the motor 46 integral with the tool is generally capable of outputting 60 Watts or more of power. This is typically two to five times the power that can be output by the motor contained in a conventional irrigator. Motor 46 therefore output more power to the pump 48 than is output by the motor of a conventional irrigator. As a result pump 48 in comparison to the pump of a conventional irrigator is able to output fluid both at a higher flow rate and in pulses that have appreciably greater impact pressures.

Still another feature of irrigator assembly 30 is that surgical tool 44 and wand 52 are separate components. This means the practitioner, with one hand, controls the on/off state of the assembly, by depressing the tool trigger 76 and, with the other hand, controls the position of the wand 52 and tip assembly 58. Often when the practitioner performs these tasks, the tool 44 is simply resting on a static surface. So even though the tool may weight in excess of 1 kg., the practitioner does not employ muscles to hold the tool in opposition to gravity. Only minimal motor skills are required to hold onto the tool 44 while simultaneously positioning the wand 52 and tip assembly 58. Since the wand and tip assembly typically weigh less than less than 0.3 kg and often less than 0.15 kg, minimal muscle power is required to hold the tip assembly against a wound or surgical site for periods of time exceeding 5 minutes. Consequently, when the practitioner has to so hold the wand and tip assembly of this invention for these extended periods of time, there the likelihood that this individual will experience muscle fatigue or strain is substantially reduced.

Further wand 52 of this invention does not have a pump trigger, a component common with conventional irrigators. This feature of the wand 52, in combination with the relatively low weight of the wand, makes it possible for the practitioner to hold the wand in unusual positions, such as straight up or straight down, without appreciably adding to the effort required to so position the wand.

Irrigator assembly 30 is also designed so that the assembly suction tube 66 extends through the pump housing 86. This minimizes the extent to which suction tube 66 moves away from complementary supply tube 50. The holding of these tubes relatively close to each other reduces the potential for other objects or the individuals attending to the patient becoming tangled in the tubes.

It is still another feature of this invention, is the pump 48 is configured to convert the rotational motion of the tool drive spindle 68 to reciprocating motion that is along an axis perpendicular to the longitudinal axis of the drive spindle. This feature of the invention serves to hold the components internal to the pump 48 to a minimum.

Figure 12:
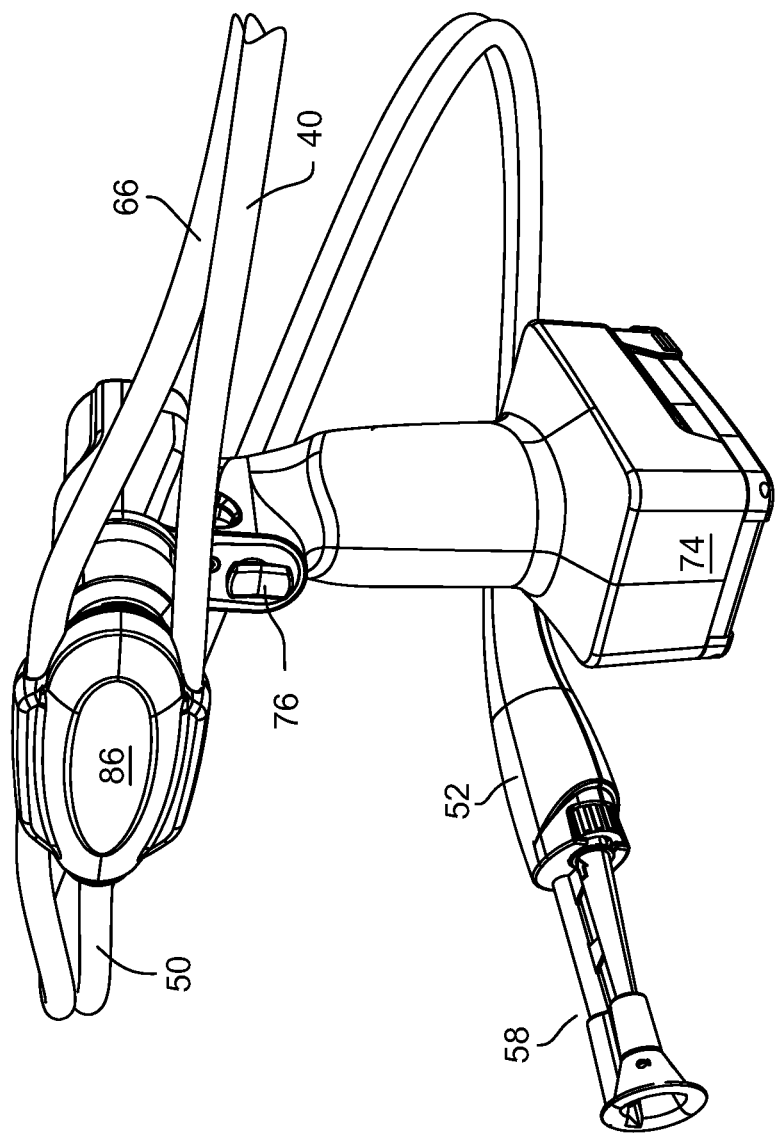
FIG. 12 depicts how the pump may be coupled to the surgical tool in an orientation different from the orientation of FIG. 1.

As seen by comparing FIG. 12 to FIG. 1, pump housing 86 of this invention is designed so that the housing can be releasably coupled to the tool 44 in plural orientations. In FIG. 1 the supply tube 50 extends from the left side of the tool 44. Here this is the "left" side of the tool 44 from the perspective of the person holding the tool. In FIG. 12 the supply tube 50 extends from the right side. This feature of assembly means that the assembly could be configured to personal preference of the individual using the assembly. If the practitioner wants to hold the tool, manipulate the trigger, using his/her right hand and position the wand with the left hand, the assembly can be set up as in FIG. 1. If the practitioner wants to hold the tool, manipulate the trigger, using his/her left hand and position the wand with the right hand, the assembly can be set up as in FIG. 12. In either configuration the tubes 40, 50 and 66 would be positioned in such a way to minimize the practitioner's entanglement with the tubes.

Post procedure, only the wand, tubing, pump and tip assembly are subject to disposal. There is no motor subject to disposal. A battery pack, which is often part of a conventional irrigator, likewise does not become an article of waste. An aspect of this feature of the invention is the current practice is to remove the batteries so they are disposed of separately from the plastic waste.

Tool 44, and only the tool, is sterilized using conventional sterilization methods. It should be understood that if the tool is battery powered, the battery 74 is of course also sterilized.

II. Second Embodiment

Figure 13:
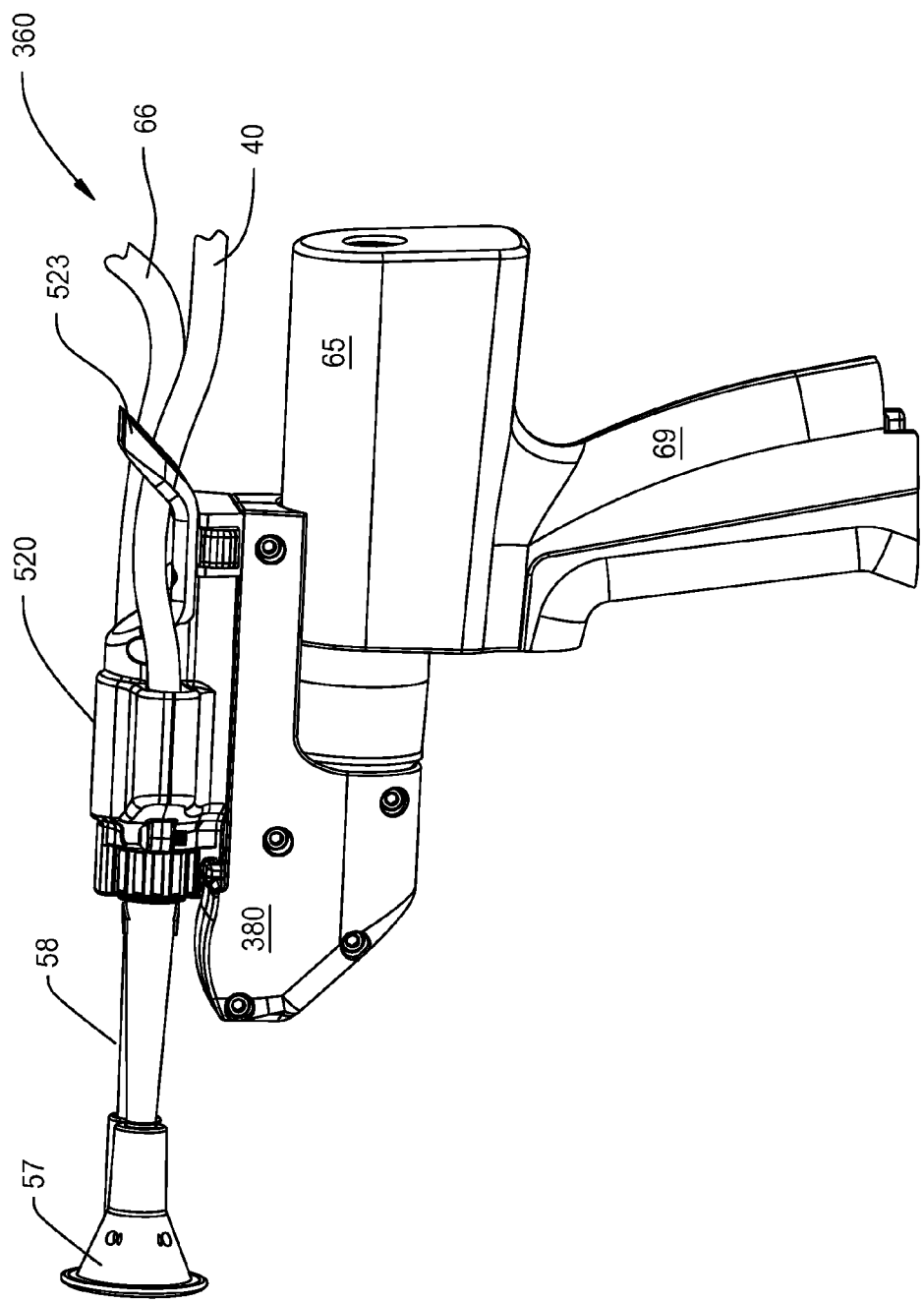
FIG. 13 is a perspective view of an alternative pump assembly of this invention.
Figure 17:
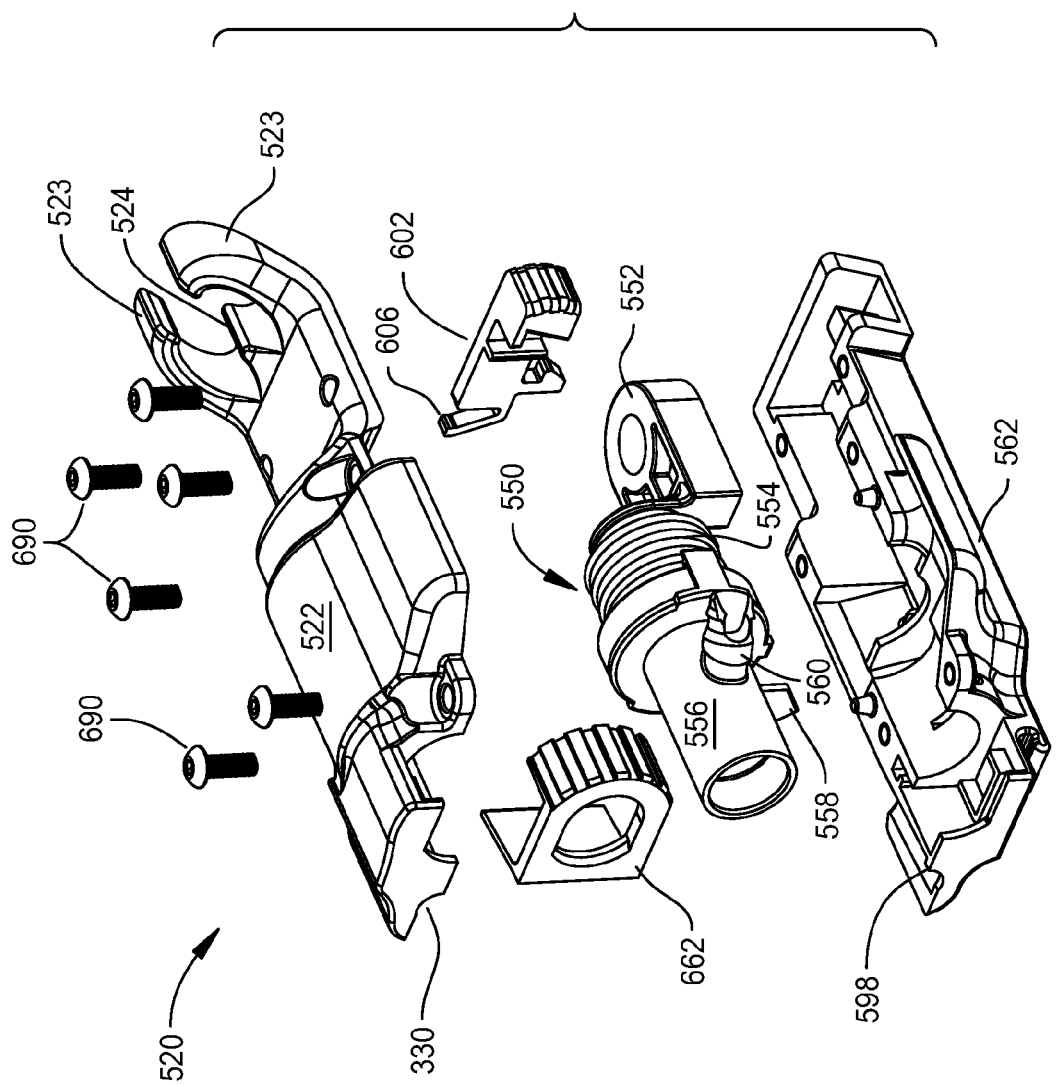
FIG. 17 is an exploded view of the pump cassette of the assembly of FIG. 13.

FIG. 13 illustrates an alternative pump assembly 360 of this invention. Assembly 360 includes tool 44, a transmission 380 and a pump cassette 520. Transmission 380 is removably attached to tool 44, (battery 74 not shown). Transmission 380 converts the rotary motion of the drive spindle 68 into a motion that reciprocates a drive pin 478. Cassette 520 is removably attached to transmission 380. Internal to cassette 520 is a pump 550 (FIG. 17). Tip assembly 58 extends forward from the cassette 520. When the cassette 520 is fitted to transmission 380, the drive pin 478 engages pump 550. Pump 550 draws irrigating fluid out of supply line 40 and forces the fluid out of the cassette and the tip assembly discharge tube 59.

Figure 14:
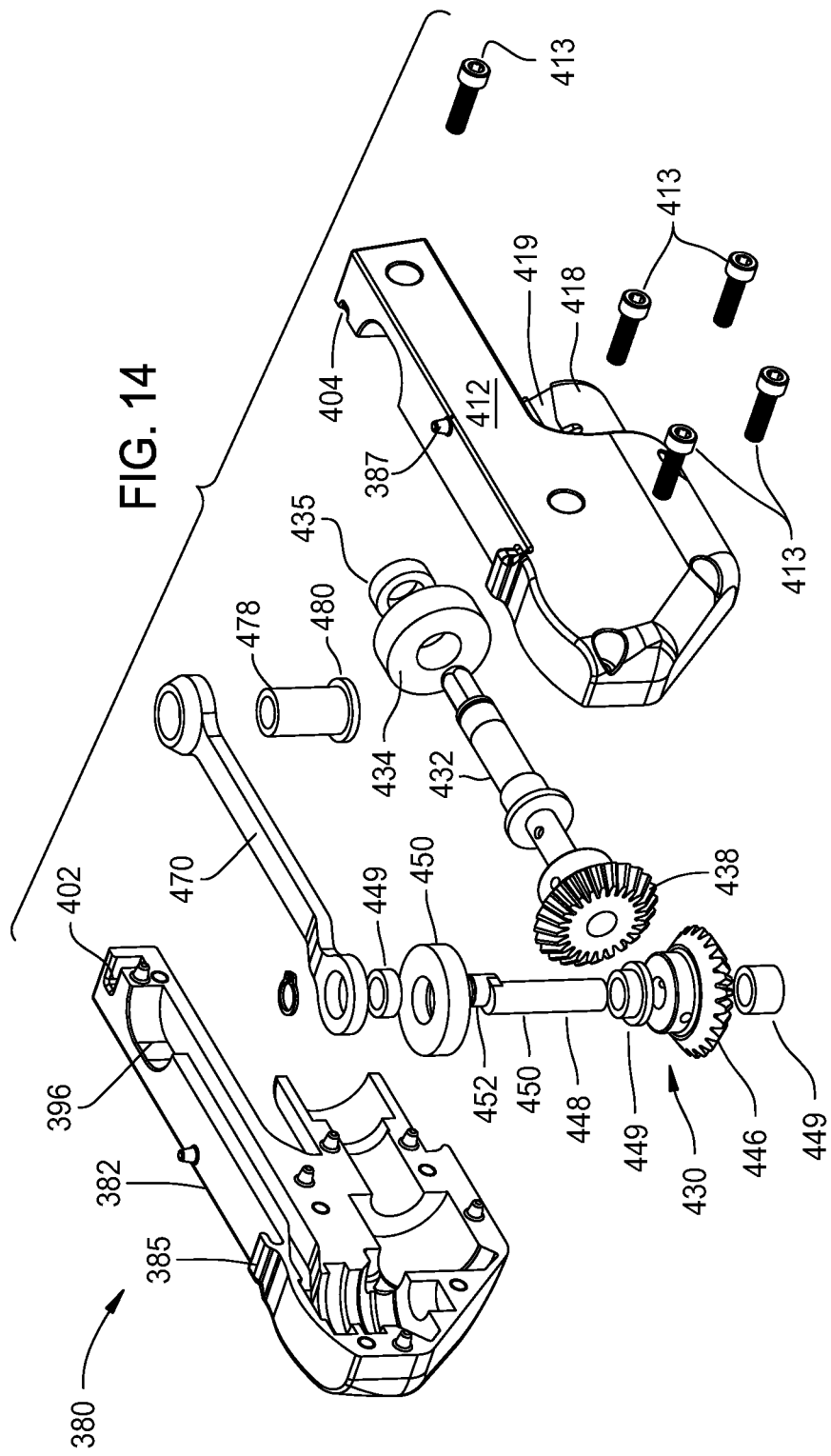
FIG. 14 is an exploded view of the transmission of the pump assembly of FIG. 13.

As seen in FIG. 14, transmission 380 includes a housing that is formed from right and left shells 382 and 412, respectively. When assembled together, the shells 382 and 412 form a sleeve 418. Sleeve 418 is dimensioned to fit in tool sleeve 73. Sleeve 418 is formed with at least one feature that, in cooperation with the coupling features integral with tool 44, facilitate the releasable attachment of transmission 380 to the tool. One of these features, a slot 419, is partially seen in FIG. 14. The transmission housing is shaped so that when the transmission is secure to the tool, the main portion of the housing is disposed on top of tool barrel 65.

Internal to the transmission housing is a gear train 430 to which a drive link 470 is connected. Drive pin 478 is connected to the proximal end of the drive link to move with the drive link 470. Gear train converts the rotary motion output by the tool drive spindle 68 into motion that reciprocates drive link 470 and drive pin 478.

Figure 15:
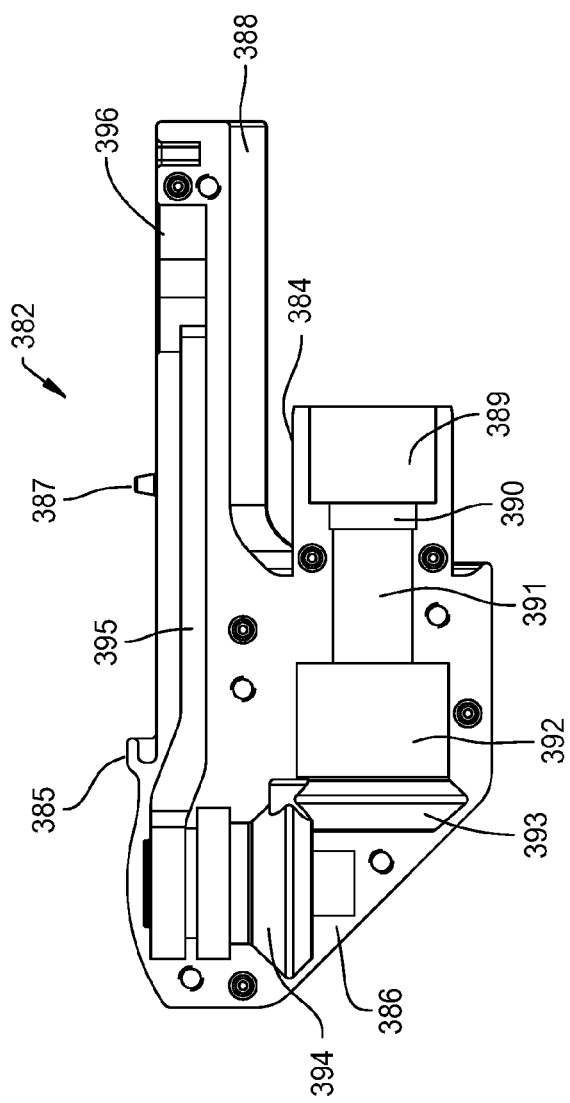
FIG. 15 is a side view of the inside of one of shells forming the housing of the transmission of FIG. 14.

FIG. 15 depicts the inside of transmission right shell 382, the left shell 412 having generally a mirror image geometry of the right shell 382. Shell 382 is formed to have a semi-circular half-sleeve 384. The half-sleeves of shells 382 and 412 collectively forming sleeve 418. Distally forward half-sleeve 384 shell 382 has a head 386. Head 386 extends outwardly from half-sleeve 384. An arm 388 extends proximally from head 386. Arm 388 is spaced above and extends proximally rearward from half-sleeve 384. When the transmission 380 is mounted to tool 44, the sleeve heads 386 are the portion of the transmission housing that are located forward of tool sleeve 73. The sleeve arms 388 are collectively the section of the transmission housing that extends over tool barrel 65. In some versions of the invention, the transmission housing is formed so that the sleeve arms 388 are disposed a small distance, typically 3 mm or less above the outer surface of the tool barrel 65.

A rib 385 extends upwardly from the shell head 386. Rib 385 is, cross section generally shaped like the upper half of the letter C. Rib 385 is spaced above arm 388 so as to extend a short distance over the distal end of arm 388. A post 387 extends upwardly from the outer surface of arm 388.

Each shell 382 and 412 is formed with a number of void spaces. A set of void spaces 389, 390, 391, 392 and 393 extend along a line coincident with the longitudinal axis of half-sleeve 384. Void spaces 389 and 390 as well as the proximal end of void space 391 are disposed in half-sleeve 384. The distal portion of void space 391 and void spaces 392 and 393 are located in shell head 386. A set of void spaces collectively identified by identification number 394 are also formed in sleeve head 386. These void spaces are centered on an axis perpendicular to the axis along which void spaces 389-393 are centered. These void spaces are generally located above void spaces 389-393. One of these void spaces intersects void space 393.

Each shell 382 and 412 is further formed to have an elongated slot 395. The slot 395 extends from the top most one of the void spaces 394 proximally so as to extend through arm 388. The distal end of the slot 395 is elevated relative to the middle and proximal sections of the slot 395. Slot 395 terminates in an opening 396 formed in the arm 388. Opening 396 opens into the top surface of the arm 388.

Transmission shells 382 and 412 are further formed to have asymmetric notches 402 and 404, respectively. Notches 402 and 404 are located immediately forward of the proximal end of arms 388. The width of notch 402, the length perpendicular to the longitudinal axis of arm 388, is greater than the width of notch 404. Arm 388 is further formed so that there is small undercut (not illustrated) integral with notch 404 below the surface of the arm 388.

Fasteners 413 are used to secure shells 382 and 412 together. Not identified are the geometric features integral with the shell 382 and 412 in which the fasteners are seated. When the shells are secured together, the void spaces 389-394 and slot 395 of shell 382 meet the complementary void spaces 389-394 and slot 395 of shell 412. The contiguous void spaces form bores internal to the transmission housing. The contiguous slots 395 form a single elongated slot below the top outer surface of the transmission housing.

Returning to FIG. 14 it can be seen that gear train 430 includes an input shaft 432. Input shaft 432 is rotatably disposed in the bore formed the transmission housing by shell void spaces 389-392. Bearing assemblies 434 and 435 rotatably hold the input shaft 432 in the transmission housing. While not identified, the proximal end of input shaft 432 includes features that engage the tool drive spindle 68 so that shaft 432 rotates with the drive spindle 68. A beveled gear 438 is mounted to the distal end of input shaft 432. Gear is disposed in the transmission housing bore formed by void spaces 393.

An output shaft 448 is also rotatably disposed in the transmission housing. Shaft 448 is disposed in the bores defined by void spaces 394. Bearings 449 and 450 rotatably hold the shaft in the transmission housing. A beveled gear 446 is disposed to the end of shaft 448 located furthest within the head of the transmission housing. Output shaft 448 is formed to have a main body 450 and a head 452 both of which are generally cylindrical. The longitudinal axis of the head 452 is laterally offset from the longitudinal axis of the main body 450. When transmission 380 is assembled, head 452 is located in the topmost bore of void space 394, the bore that intersects the void space internal to the transmission head formed by the contiguous slots 395.

Figure 16:
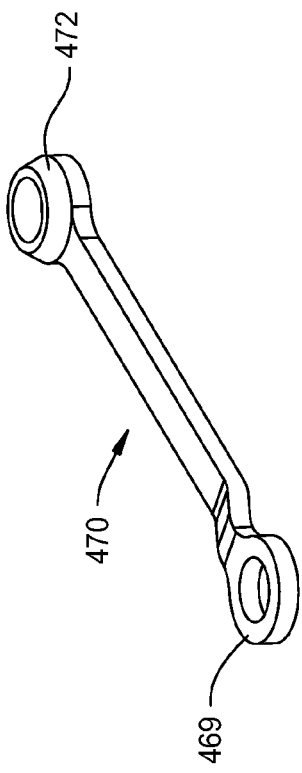
FIG. 16 is a perspective view of the transmission drive link.

From FIG. 16 it can be seen that drive link 470 is generally in the form of an elongated bar. A ring 469 is located at the distal end of the link. Ring 469 is elevated and parallel to the main body of the body of the link. Not identified is the angled front end of the bar that forms the transition from ring 469 to the main body of the bar. Link 470 is further formed to have a proximal end ring 472. When the transmission is assembled, link 470 is slidably disposed in the void space formed by the contiguous shell elongated slots 395. Distal end ring 469 is seated over the head 452 of output shaft 448. The proximal end ring 472 is seated below the opening 396 formed in the transmission housing.

Drive pin 478 is generally in the form of cylindrical structure. A lip 480 extends radially outwardly and circumferentially around the base of the pin. Drive pin 478 extends through the opening integral with the proximal end ring 472 integral with the drive link 470. In some versions of the invention, pin 478 is press fit through ring 472. The drive pin 478 extends out through the transmission housing opening 396 so as to project above the transmission housing Cassette 520, as seen in FIG. 17, includes a housing that consists of top and bottom shells 522 and 562, respectively. Internal to the cassette housing is a moveable latch 602, pump 550 and a tip lock 662. Latch 602 seats in notches 402 and 404 to releasably hold the cassette 520 to the transmission 380. When the cassette 520 is so secured, transmission drive pin 478 extends through an opening 570 in bottom shell 562. The drive pin 478 engages pump 550. Tip lock 662 releasably holds tip assembly 58 to the cassette 520.

Top shell 522 is formed to have at the proximal end, a pair of curved feet 523. Feet 523 are symmetric along a plane extending vertically through the longitudinal axis of the shell 522. Each foot 523 extends from an outer side of the shell 522 and curves inwardly towards the center of the shell. The ends of the feet 523 are spaced apart from each other. Top shell 522 is further formed to have rib 524 that extends upwardly from the surface of the shell. Rib 524 is located between feet 523. The rib 524 is shaped to have opposed longitudinally extending outer surfaces that have a concave curvature, (surfaces not identified). Feet 523 and rib 524 are spaced apart from each other so supply tube 40 can be held, lightly compressed between one foot 523 and the rib and suction tube 66 can similarly be held between the other foot 523 and the rib.

Figure 18:
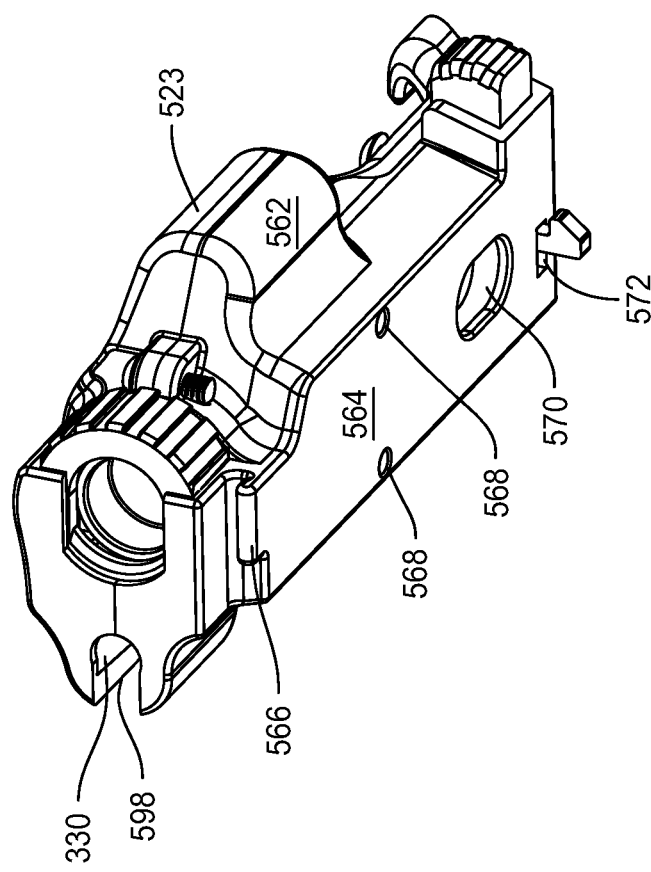
FIG. 18 is a perspective view of the pump cassette.

As seen best in FIG. 18, cassette bottom shell 562 has a planar base surface 564. The cassette bottom shell 562 is dimensioned to seat on the adjacent outer surfaces of the arms 388 integral with transmission 380. A lip 566 projects forward from and the shell base surface 564. Lip 566 is dimensioned to closely slip fit within the space between the transmission housing ribs 385 and underlying arms 388. Bottom shell 562 is further formed so that there are two small diameter circular openings 568 in base surface 564. When cassette 520 is seated on transmission 380, each transmission post 387 seats in a separate one of the cassette openings 568. The bottom shell 562 is further formed so that, slightly forward of the proximal end of the shell there is an oval opening 570. The major axis of opening 570 is parallel to if not aligned with the longitudinal axis of pump 550. Opening 570 is positioned and dimensioned to receive drive pin 478. The opening 570 is further dimensioned so that the drive pin 478 can move longitudinally in the opening 570.

Cassette bottom shell 562 is further formed to have an opening 572. Opening 572 is located between the proximal end of the shell 562 and opening 570. The bottom shell 562 is formed so that opening 572 is rectangular in shape and orientated so that the major axis of the opening is perpendicular to the longitudinal axis of the cassette 520. The cassette 520 is further shaped so that when the cassette 520 is mounted to the transmission 380 opening 572 extends at least partially over the opening formed by notches 402 and 404 integral with the transmission 380.

Figure 19:
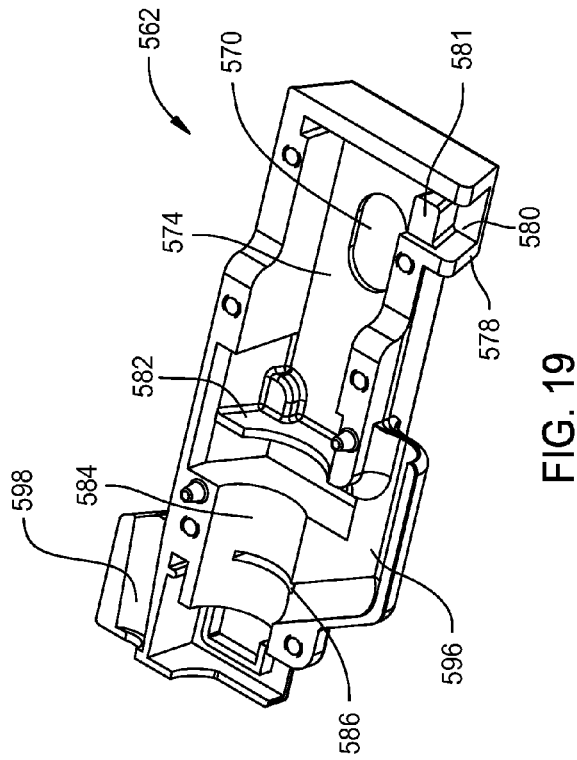
FIG. 19 is a perspective view of the inside of the bottom shell of the pump cassette.
Figure 20:
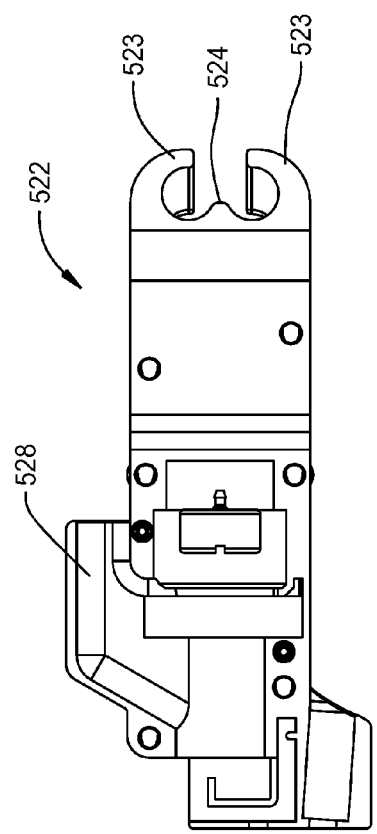
FIG. 20 is a plan view of the inside of the top shell of the pump cassette.

As seen in FIG. 19, internal to the bottom shell 562 there is a generally rectangular void space 574. Openings 570 and 572 open into void space 574. Immediately forward of the proximal end of the shell 562 a three sided frame 578 extends laterally away from one side of the shell. Frame 578 defines a recess 580. Inward of frame 578 the shell has a web 581. Web 581 defines the base of recess 580. Web 581 does not extend completely across the frame 578. Instead, the web terminates distal to the proximal end wall of the shell 562. Consequently, there is a small gap between the proximal end wall of the shell 562 and web 581, (gap not identified).

A web 582 with an arcuate cutout (not identified), extend into void space 574. Distally forward of void space 574, bottom shell is formed with an inwardly shaped arcuately recessed surface 584. A rectangular slot 586 extends inwardly from surface 584. The major axis of slot 586 is perpendicular to the longitudinal axis through the shell 562.

Figure 21:
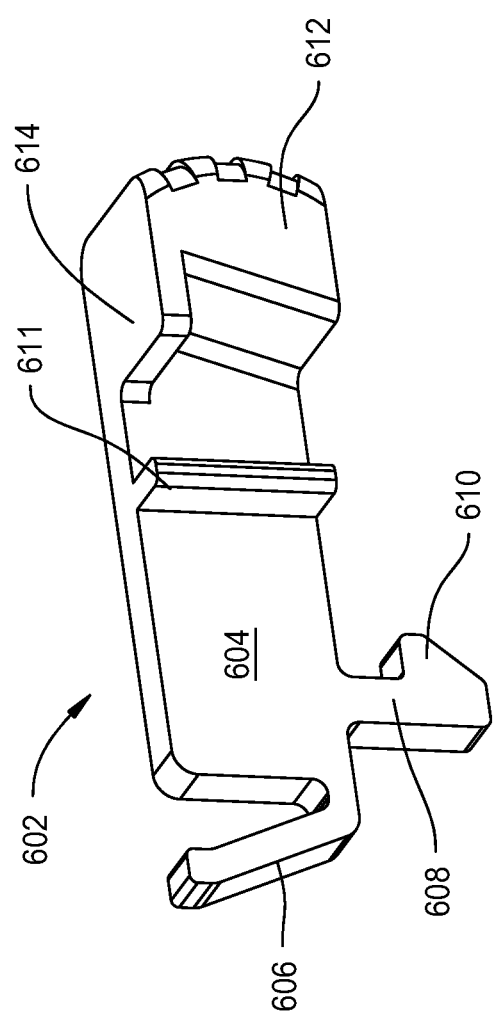
FIG. 21 is a perspective view of the latch internal to the pump cassette.

Latch 602, as seen in FIG. 21, is formed from a single piece of plastic. The latch has a main body 604, of generally rectangular shape. A first foot, foot 606 extends away from one end of the body 604 so as to extend across and away from the end of the body to which the foot is attached. Foot 606 is able to flex relative to body 604. A second foot, foot 608 extends outwardly from one of the side edges of the body. More particularly foot 608 extends away from the side of the body 604 from which foot 606 extends. Foot 608 is formed with a toe 610 that extends forward from the portion of the foot that extends away from the latch main body 602.

The latch 602 is further formed to have a rib 611. Rib 611 extends laterally across the main body 604. Rib 611 extends across the latch main body 604 at a location close to the end of the main body opposite the end of the body from which foot 606 extends. Latch 602 also has a head 612. The head extends outwardly from the major surface of the body 604 from which rib 610 extends. A reinforcing web 614 extends from a side edge of the main body 604 to head 612.

Latch 602 is slidably mounted in cassette bottom shell 562. More particularly, the latch is mounted within the shell 562 so that the flat, featureless main surface of the latch main body 604 is disposed against the inner surface of the proximal wall of the shell 562. Foot 606 abuts the inner surface of the side wall opposite the side of the shell from which frame 578 extends. Foot 610 extends out of shell opening 572. The end of latch main body 604 opposite foot 606 extends through the gap between the shell proximal wall and 581. Latch head 612 is seated in recess 580.

Owing to the dimensioning of bottom shell 562 and latch 602, foot 606 normally places a force on the rest of the latch 602 that pushes the rest of the latch away from the side wall of the shell against which the foot 606 abuts. The outward movement of the latch 602 is limited by the abutment of latch rib 611 against the inner surface of shell web 581.

Pump 550 is generally similar in structure to previously described pump 48. The yoke 552 and bellows 554 of pump 550 are disposed in the void space of bottom shell void space 574. The pump static tube 556 is seated against shell recessed surface 584. The tab 558 integral with the outer tube seats in shell slot 586.

Tip lock 662 is moveably mounted to shells 522 and 562 in a space immediately proximal to the front face of the cassette housing formed by the shells.

From FIG. 13 it can be seen that supply tube 40 is seated between the left side foot 523 and rib 524. While not illustrated it should be understood the supply tube 40 extends into the cassette housing through the channel defined top and bottom shell grooves 528 and 596, respectively. The distal end of the supply tube is attached to the fitting 560 integral with pump static tube 556.

A suction tube, not illustrated, is sandwiched between shells 522 and 562. The suction tube extends from a location adjacent the opening in a distally directed wall of the top cassette housing into which the tip assembly suction tube 64 is seated. The suction tube extends substantially linearly through the cassette housing. The suction tube extends proximally out of the housing through the bore formed by top and bottom shell grooves 330 and 598, (FIG. 18) respectively.

Fasteners 690 hold shells 522 and 562 together. Not identified are the geometric features of the shells 522 and 562 in which the fasteners 690 are seated.

Assembly 360 is readied for use by first fitting transmission 380 to the tool 44. Cassette 520 is fitted over the transmission 380. This process is initially performed by seating the cassette lip 566 into the void space below transmission ribs 385. This serves to secure the distal end of the cassette 520 to the transmission 380. The cassette is pivoted downwardly to cause transmission pins 37 to seat in cassette bores 568. The continued movement of the cassette 520 against the transmission results in latch toe 610 seating in the undercut integral with transmission notch 404. During this part of the attachment process foot 606 is momentarily compressed. This engagement releasably holds the cassette 520 to the transmission 380. As a consequence of this positioning of the cassette 520, transmission drive pin 478 seats in pump yoke 552.

The assembly is positioned so that the tip assembly 58 is located adjacent the site to which the irrigating fluid is discharged. Tool trigger 76 is depressed. The resultant actuation of the tool motor 46 results in the actuation of cassette pump 550. The actuation of the pump 550 results in the discharge of the irrigating fluid from discharge tube 59.

Once assembly 360 is used in a procedure, the cassette 520 is removed from the transmission 380 for disposal of the cassette. To decouple the cassette 520 from transmission 380, finger force is applied against latch head 612. This finger force overcomes the spring force of foot 606 so as to cause the displacement of the latch. The displacement of the latch withdraws toe 610 from the undercut in the transmission in which the toe is seated. This repositioning of latch 602 allows the cassette 520 to be lifted off the transmission.

Assembly 360 is constructed so that the transmission 380 is disposed above the tool 44 and the cassette 520 is disposed above the transmission. This means that the center of gravity of the assembly, the tool 44, the transmission, 380, the cassette 520 and the tip assembly 58 are located relatively close to the handgrip 69, the portion of the assembly held and manipulated by the practitioner. Ergonomically, this reduces the muscle strain to which the practitioner is exposed when holding the assembly 380 against a site for an extended period of time.

Similarly it should be understood that in this version of the invention, the distal end of the tip assembly is typically located a maximum of 30 cm from the front of the handgrip 69 (along a longitudinal axis through the assembly). More preferably this distance is at the most 25 cm and still even more preferably no more than 20 cm. One advantage of the assembly 360 of this invention being compact in this dimension is that it reduces the efforts required to position the distal end of the tip assembly when the practitioner has to target surfaces that are relative to the practitioner chest high or higher. This type of positioning is known to occur when an irrigator is used to clean tissue in a total knee replacement procedure and the knee is in flexion.

Further there is still a further benefit of the assembly 360 of this version of the invention being compact along this axis. The suction drawn through tip assembly 58 and cartridge 520 can be of sufficient strength to cause the tip assembly to essentially adhere to the tissue to which the assembly is applied. If there is an appreciable distance between this interface and the handgrip 69, when it is desirable to shift the position of the tip assembly, the practitioner may have to apply a significant amount of torque to the handgrip to overcome the resistive suction force. If this distance is relatively short, less torque is applied to the tool handgrip 69 so reposition the tip assembly 58.

Still another feature of this version of the invention is that in the cassette there is substantially no bending of the suction tube in the cassette. The longitudinal axis through the distal most 2 cm of the tube within the cassette is offset by less than 30° and often less than 10° from the longitudinal axis through the proximal most 2 cm of the tube. In many versions of the invention, the suction tube extends linearly through the cassette 520. The length of the section of the tube within the cassette, the section to which the tip assembly suction tube 64 is attached, has a length of at least 10 cm. Since there is minimal or no bending of the suction tube within this section of the suction tube, there are essentially no bends that can serve as locations where debris entrained in the waste stream withdrawn from the site through assembly 360 can clog the suction line. Further the straight through or at least essentially straight flow suction ensures a high flow rate as compared to the flow rate through the same length of tube that is appreciably bent.

As with the first embodiment of the invention the presence of the suction tubes eliminates the need to provide a separate suction wand for collecting the fluid discharged by the irrigator assembly of this invention.

The presence of the tip lock reduces the likelihood that during the procedure the tip assembly 58 will inadvertently separate from the cassette 520. If this separation occurs during the procedure, the separation could result in an uncontrolled release of irrigating fluid. This fluid could contaminate the surrounding environment. The fluid could potentially even contaminate the surgical site to which the irrigating fluid was being applied.

Cassette 520 is further positioned to minimize the likelihood that the tubes connected to the cassette will somehow approach the tool handgrip 69. This reduces the likelihood that the tubes will somehow come so close to the trigger that they will interfere with the practitioner's actuation of the trigger.

In many versions of this invention, transmission 380, the sub-assembly through which fluid is not flowed, is formed out of components that are sterilizable. The pump 520, which is the sub-assembly through which fluid is flowed is formed out of components that are often not sterilizable. Generally, it is more expensive to construct a device through which fluid is flowed out of sterilizable components. Thus, am additional feature of many versions of pump assembly 360 is that it can be more economical to provide the transmission 380 of this invention and sterilize the transmission for reuse than to provide with a transmission formed out of non-sterilizable components that is designed for a single use.

II. Alternative Embodiments

It should be appreciated that the above is directed to specific versions of the invention. Alternative irrigating assemblies of this invention may be proved.

The features of the different versions of this invention may be combined. For example, wand 52 of the first embodiment can be added to the assembly 360 of the second embodiment, Alternatively not all versions of this invention may use each of the features disclosed with regard to the two described versions of the invention.

For example, there is no requirement that the tool integral with the system be a battery powered power tool. The system of this invention may include an electrically driven power tool that receives its power from a remote console over a cord. Alternatively, the tool integral with this system may include a pneumatically or hydraulically driven motor.

Also, it is often desirable to attach a clamp to the suction tube 66. This clamp is selectively closed to prevent suction drawn when it is not desired by the practitioner. When suction is not desired this also minimizes suction noise. Further, negating the suction draw can, in some situations reduce the extent to which airborne contaminates are drawn towards the site to which the tip assembly is applied.

Similarly, while seldom employed, some irrigators of this invention may not include a means for drawing discharged fluid from the site to which the irrigating fluid is discharged. This would eliminate the need to provide the suction tube 66 and like features for holding the suction tube to the rest of the assembly. In versions of the assembly in which the suction tube 66 is present, it may not always be necessary to thread the suction tube through the pump housing.

In many versions of the invention, supply tube 50 and suction tube 66 may be bonded or clipped together. Holding these tubes in tandem reduces the likelihood of these tubes tangling with each other, other equipment or the practitioner. For the same reason at least the section of supply tube 40 adjacent the pump and the adjacent section of the suction tube 66 may likewise be bonded or clipped together. In these and outer versions of the invention there might not be a need to thread the suction tube through the pump housing 86.

There is no requirement that all versions of the invention the wand and tip assembly be separate components. In versions of the invention in which these components are a unified assembly the need to provide a tip fitting and or tip lock may be eliminated.

Further it may be necessary to form supply tube 50 out of homogenous plastic that has the desirable modulus of elasticity, that resists radial deformation. Supply tube 50 can be formed out of tube with internal braiding or fibers that resist radial expansion. For economics of manufacture, it may not be necessary to supply tube 40 or the suction tube 66 out of material that is as radially stiff as supply tube 50.

Likewise, the type of pump integral with this invention is not limited to bellows pump. Other positive displacement pumps such as piston pumps or pumps with a diaphragm may be incorporated into this invention. Similarly this invention is not limited to a pump wherein the moving element reciprocates back and forth. Some versions of this invention may include pumps wherein the pumping element engages in rotary motion. Examples of such pumps are vane pumps and impeller pumps. Further in some versions of the invention the pump may be a peristaltic pump.

Each of the above types of pumps it is understood may have a transmission assembly different from what has been disclosed to convert the rotary output of the tool into motion that drives the pump. For example in some versions of the invention wherein the pump has a rotary pumping element, the transmission assembly may include a set of gears that decrease the speed/increase the torque that is applied to the pumping element.

Likewise, in some versions of the invention the transmission may actual rest on the surface of the housing of the tool to which transmission is removably attached.

Further while the suction tube may extend linearly or substantially linearly through the wand or cassette, there is no requirement that the tube extend along an axis or lie in a plane that is parallel to the longitudinal axis of the wand or cassette.

Other means than the disclosed fasteners may be used to secure the various shells together that form the housings of the components of this invention. For example, snap fasteners, adhesives and welding may be employed to hold the components of this invention together. Likewise, there is no requirement that the shells that are substantially mirror versions of each other always be mirror versions of each other.

Similarly, in versions of the invention wherein the pump and associated transmission are mounted to the top of the handpiece 44, there is no requirement that these two sub-assemblies have separate housings. In some versions of this invention these sub-assemblies may be contained in a single housing. This housing as well as the components it contains, may be either sterilizable and reusable or a single use disposable device.

Likewise, in versions of the invention wherein the pump and transmission assembly are configured to extend at least partially over the associated tool 44, there is no requirement that the pump always be seated on top of the transmission assembly. In some versions of the invention, the pump components may be substantially linearly aligned with at least some of the transmission components.

In versions of the invention wherein at least some of the components are replaceable, these components may be removably seated in a cavity formed in the housing of the transmission assembly.

Accordingly, it is an object of the appended claims to cover all such variations and modifications that come within the true spirit and scope of this invention.

What is claimed is:

1. A medical/surgical irrigating assembly, said assembly including:
    a powered surgical tool including: a body; a motor disposed in the body; a coupling feature adapted to engage an implement that performs a medical/surgical task so to hold the implement to the body; and a drive spindle connected to the motor to be actuated by said motor, said drive spindle configured for attachment to the implement so that the implement is driven by the drive spindle; and
    an irrigator, said irrigator including:
        a pump unit, said pump unit including: a pump housing, said pump housing having at least one coupling feature that cooperates with the surgical tool coupling feature to releasably hold the pump housing to the surgical tool; and a pump disposed in said pump housing for receiving irrigation fluid and pumping irrigation fluid through said pump housing, said pump including a drive shaft configured for releasable attachment to said drive spindle of said surgical tool so that the actuation of said surgical tool drive spindle results in the like actuation of said pump drive shaft;
        a tip assembly separate from said pump housing so that said tip assembly is moveable relative to said pump housing and the surgical tool; and
        a flexible first supply tube that extends from said pump housing to said tip assembly so as to provide a fluid conduit for the irrigation fluid pumped by said pump to said tip assembly so that the irrigation fluid is discharged through said tip assembly.

2. The medical/surgical irrigating assembly of claim 1, further including a suction tube, said suction tube extending from said tip assembly and adapted for connection to a device capable of drawing a suction through said suction tube.

3. The medical/surgical irrigating assembly of claim 2, wherein said suction tube is attached to said pump housing so as to move with said pump housing and extends from said pump housing to the device that draws a suction.

4. The medical/surgical irrigating assembly of claim 2, wherein a portion of said suction tube extends through said pump housing and extends from said pump housing to the device that draws a suction.

5. The medical/surgical irrigating assembly of claim 1, further including a wand shaped to be hand held to which a distal end of said first supply tube is attached so that said wand is moveable relative to said pump housing and said surgical tool and wherein said tip assembly is removably attached to said wand.

6. The medical/surgical irrigating assembly of claim 1, wherein said pump is configured to discharge the irrigating fluid in pulses.

7. The medical/surgical irrigating assembly of claim 1, wherein said pump includes at least one component in said pump housing that converts rotary motion of said pump drive shaft into motion that reciprocates said pump.

8. The medical/surgical irrigating assembly of claim 1, wherein said at least one pump housing coupling feature is an indentation formed on the pump housing.

9. The medical/surgical irrigating assembly of claim 1 wherein:
    said pump housing includes a sleeve dimensioned to seat in an opening of the powered surgical tool; and
    said pump drive shaft is mounted to said pump housing so as to at least partially extend through said sleeve of said pump housing.

10. The medical/surgical irrigating assembly of claim 9, wherein said at least one pump housing coupling feature is formed on said sleeve.

11. The medical/surgical irrigating assembly of claim 1, wherein:
a second supply tube separate from said first supply tube extends from a source of irrigating fluid to said pump; and
both said first supply tube and said second supply tube have a modulus of elasticity such that said tubes resist radial expansion, said tube having moduli of elasticity that are different such that said first supply tube resists radial expansion more than said second supply tube.

12. The medical/surgical irrigating assembly of claim 1, wherein:
said first supply tube extends laterally outwardly from a side of the pump housing; and
the powered surgical tool coupling feature and said pump housing coupling feature are collectively configured to allow said pump housing to be connected to the surgical tool in a plurality of different orientations so that the direction from which said first supply tube extends outwardly from the surgical tool can be selectively set.

13. The medical/surgical irrigating assembly of claim 1, wherein said motor of said powered surgical tool is one of: electrically driven; pneumatically driven; or hydraulically driven.

14. The medical/surgical irrigating assembly of claim 1 wherein:
said motor of said powered surgical tool is electrically driven; and
a battery is removably connected to said powered surgical tool for providing charge to said motor.

15. An irrigator for use with a powered surgical tool, the powered surgical tool including a motor, a surgical tool coupling feature, and a drive spindle that is driven by the motor for releasable connection to an implement capable of performing a medical/surgical task, said irrigator including:
a pump unit, said pump unit including: a pump housing, and a pump disposed in said pump housing for pumping irrigation fluid through said pump housing, said pump including a drive shaft configured for releasable attachment to the drive spindle of the surgical tool so that the actuation of the surgical tool drive spindle results in the like actuation of said pump drive shaft;
a flexible first supply tube having opposed ends, a first end of said first supply tube being connected to said pump for receiving the irrigation fluid discharged from said pump and extending outwardly from a side of said pump housing;
said pump housing having at least one coupling feature for cooperating with the surgical tool coupling feature to releasably hold said pump housing to the surgical tool; and
a tip assembly separate from said pump housing so that said tip assembly is moveable relative to said pump housing and the surgical tool wherein the second end of said first supply tube is in fluid communication with said tip assembly so that the irrigation fluid that flows through said first supply tube will be discharged through said tip assembly.

16. The irrigator of claim 15, further including a suction tube that extends from said tip assembly that is adapted for connection to a device capable of drawing a suction through said suction tube, wherein said suction tube is attached to said pump housing to move with said pump housing and extends from said pump housing to the device that draws a suction.

17. The irrigator of claim 15, wherein:
said first supply tube extends from said pump housing to a wand, said wand being separate from said pump housing so that said wand is capable of movement relative to said pump housing; and
said tip assembly is removably attached to said wand so that the attachment of said tip assembly to said wand results in the connection of said first supply tube to said tip assembly.

18. The irrigator of claim 15, wherein said pump is configured to discharge the irrigating fluid in pulses.

19. The irrigator of claim 15, wherein said at least one coupling feature is an indentation formed in said pump housing.

20. The irrigator of claim 15, wherein said pump housing is formed with plural spaced apart indentations, the indentations functioning as separate said coupling features.

21. The irrigator of claim 15, wherein a second supply tube separate from said first supply tube extends from a source of irrigating fluid to said pump.

22. The irrigator of claim 21, wherein both said first supply tube and said second supply tube have a modulus of elasticity such that said tubes resist radial expansion, said tube having moduli of elasticity that are different such that said first supply tube resists radial expansion more than said second supply tube.

23. The irrigator of claim 15, wherein:
said pump housing is formed to have a sleeve dimensioned to seat in an opening of the surgical tool to which said pump housing is attached; and
said pump drive shaft is disposed in said pump housing sleeve.

24. The irrigator of claim 15, wherein:
said pump housing is formed to have a sleeve dimensioned to seat in an opening of the surgical tool to which said pump housing is attached;
said at least one coupling feature is formed on said pump housing sleeve; and
said pump drive shaft is disposed in said pump housing sleeve.

* * * * *